US007745532B2

(12) United States Patent
Ruberti et al.

(10) Patent No.: US 7,745,532 B2
(45) Date of Patent: Jun. 29, 2010

(54) SYSTEMS AND METHODS FOR CONTROLLING AND FORMING POLYMER GELS

(75) Inventors: Jeffrey W. Ruberti, Lexington, MA (US); Gavin J. C. Braithwaite, Cambridge, MA (US)

(73) Assignee: Cambridge Polymer Group, Inc., Boston, MA (US)

( * ) Notice: Subject to any disclaimer, the term of this patent is extended or adjusted under 35 U.S.C. 154(b) by 152 days.

(21) Appl. No.: 10/631,491

(22) Filed: Jul. 31, 2003

(65) Prior Publication Data
US 2004/0092653 A1 May 13, 2004

Related U.S. Application Data

(60) Provisional application No. 60/400,899, filed on Aug. 2, 2002.

(51) Int. Cl.
C04B 24/26 (2006.01)
C08G 73/06 (2006.01)

(52) U.S. Cl. ........................ 524/803; 524/881

(58) Field of Classification Search ................ 524/630, 524/803, 881
See application file for complete search history.

(56) References Cited

U.S. PATENT DOCUMENTS

| 3,875,302 | A | 4/1975 | Inoue | 426/1 |
|---|---|---|---|---|
| 4,472,542 | A | 9/1984 | Nambu | 523/309 |
| 4,663,358 | A | 5/1987 | Hyon | |
| 4,772,287 | A | 9/1988 | Ray et al. | 623/17 |
| 4,904,260 | A | 2/1990 | Ray et al. | 623/17 |
| 5,047,055 | A | 9/1991 | Bao et al. | 623/17 |
| 5,071,437 | A | 12/1991 | Steffee | 623/17 |
| 5,091,121 | A | 2/1992 | Nakada et al. | 264/1.4 |
| 5,260,066 | A | 11/1993 | Wood et al. | 424/447 |
| 5,288,503 | A | 2/1994 | Wood et al. | 424/497 |
| 5,385,606 | A | 1/1995 | Kowanko | 106/124 |
| 5,534,028 | A | 7/1996 | Bao et al. | 623/17.16 |
| 5,705,296 | A * | 1/1998 | Kamauchi et al. | 429/330 |
| 5,731,005 | A | 3/1998 | Ottoboni | |
| 5,880,216 | A | 3/1999 | Tanihara | |

(Continued)

FOREIGN PATENT DOCUMENTS

EP 1229873 8/2002

(Continued)

OTHER PUBLICATIONS

AAOS, Musculoskeletal Conditions in the U.S., Feb. 1992-1988, 1992, AAOS.

(Continued)

Primary Examiner—William K Cheung
(74) Attorney, Agent, or Firm—Perkins Coie LLP

(57) ABSTRACT

The preferred embodiments of the present invention provide polymer compositions and methods for controlling a property of a resultant gel. A preferred method includes dissolving a vinyl polymer in a first solvent to form a solution; and contacting the vinyl polymer solution in a suitable volume of at least one immersion solvent comprising a second solvent to cause gelation. In preferred embodiments, the invention provides poly(vinyl alcohol) compositions and methods that produce physically crosslinked hydrogels that have tunable physical properties. Also provided are articles of manufacture such as prosthetic intervertebral disks and contact lenses.

27 Claims, 11 Drawing Sheets

U.S. PATENT DOCUMENTS

| | | | |
|---|---|---|---|
| 5,976,186 A | 11/1999 | Bao et al. | 623/17 |
| 5,981,826 A | 11/1999 | Ku et al. | 623/11 |
| 6,165,201 A | 12/2000 | Sawhney et al. | 606/214 |
| 6,231,605 B1 | 5/2001 | Ku | 623/11.11 |
| 6,264,695 B1 | 7/2001 | Stoy | 623/17.11 |
| 6,268,405 B1 | 7/2001 | Yao et al. | 523/113 |
| 6,281,264 B1 | 8/2001 | Salovey et al. | 523/115 |
| 6,423,333 B1 | 7/2002 | Stedronsky et al. | 424/423 |
| 6,520,992 B1 | 2/2003 | Zollner et al. | 623/17.16 |
| 6,592,999 B1 | 7/2003 | Anderson et al. | 428/447 |
| 6,719,797 B1 | 4/2004 | Ferree | 623/17.16 |
| 7,001,431 B2 | 2/2006 | Bao et al. | 623/17.12 |
| 7,098,194 B2 | 8/2006 | Chenite et al. | 514/55 |
| 7,214,245 B1 | 5/2007 | Marcolongo et al. | 623/17.16 |
| 7,485,670 B2 | 2/2009 | Ruberti et al. | |
| 2004/0092653 A1 | 5/2004 | Ruberti | |
| 2004/0171740 A1 | 9/2004 | Ruberti | |
| 2005/0112186 A1 | 5/2005 | Devore et al. | |
| 2005/0288789 A1 | 12/2005 | Chaouk et al. | |
| 2006/0270781 A1 | 11/2006 | Ruberti et al. | |
| 2007/0054990 A1 | 3/2007 | Ruberti et al. | |
| 2007/0100349 A1 | 5/2007 | O'Neil et al. | |
| 2007/0167541 A1 | 7/2007 | Ruberti et al. | |

FOREIGN PATENT DOCUMENTS

| | | |
|---|---|---|
| JP | 03215417 A | 9/1991 |
| JP | 04 338326 A | 11/1992 |
| WO | WO 01/12107 A1 | 2/2001 |
| WO | WO 02/054978 A2 | 7/2002 |

OTHER PUBLICATIONS

Choi, J. H., et al., "Rheological Properties of Syndiotacticity-Rich Ultrahigh Molecular Weight Poly(vinyl alcohol) Dilute Solution," Journal of Applied Polymer Science, vol. 82, 569-576 (2001).

Damshkaln, L. G., et al, Study of Cryostructuration of Polymer Systems. XV. Freeze-Thaw-Induced Formation of Cryoprecipitate Matter from Low-Concentrated Aquenous Solutions of Poly(vinyl alcohol), Journal of Applied Polymer Science, vol. 74, 1978-1986 (1999).

Darwis, D., et al, "Characterization of poly(vinyl alcohol) hydrogel for prosthetic intervetebral disc nucleus," Radiation Physics and Chemistry 63 (2002) 539-542.

de Gennes, P.-G., "Scaling Concepts in Polymer Physics," First ed. 1979: Cornell University Press, 72, 113-114.

Elias, H.G., "Theta Solvents," Brandrup, J. and E. H. Immergut, Polymer Handbook 3rd Ed., John Wiley & Sons, NY 1989.

Flory, P.J., "Principles of Polymer Chemistry," 1953, Ithaca and London: Cornell University Press.

Hassan, C., M., & Peppas, N.A., "Cellular PVA Hydrogels Produced by Freeze/Thawing," Journal of Applied Polymer Science, vol. 76, 2075-2078 (2000).

Hassan C., M. et al, "Diffusional characteristics of freeze/thawed poly(vinyl alcohol) hydrogels: Applications to protein controlled release from multilaminate devices," European Journal of Pharmaceutics and Biopharmaceutics 49 (2000) 161-165.

Hassan, C., M. et al., "Modeling of crystal dissolution of poly(vinyl alcohol) gels produced by freezing/thawing process," Polymer 41 (2000) 6729-6739.

Hickey, A. S. & Peppas N.A., "Solute diffusion in poly(vinyl alcohol)/poly(acrylic acid) composite membranes prepared by freezing/thawing techniques," Polymer, vol. 38 No. 24 1997 5931-5936.

Hong, P. et al, "Effects of Mixed Solvent on Gelation of Poly(vinyl alcohol) Solutions," Journal of Applied Polymer Science, vol. 79, Issue: 6, Date: Feb. 7, 2001, pp. 1113-1120.

Juarez, K.K. & An, H.S., "Artificial Disc Replacement," Spineuniverse.com.

Li, J. K., et al, "Poly(vinyl alcohol) nanoparticles prepared by freezing-thawing process for protein/peptide drug delivery," Journal of Controlled Release 56 (1998) 117-126.

Lozinskii V. I. & Savina I. N., "Study of Cryostructuring of Polymer Systems: 22. Composite Poly(vinyl alcohol) Cryogels Filled with Dispersed Particles of Various Degrees of Hydrophilicity/Hydrophobicity," Colloid Journal, vol. 64, No. 3, 2002, 336-343.

Lozinsky, V. I., et al, "Study of Cryostructuration of Polymer Systems, XIV. Poly(vinyl alcohol) Cryogels: Apparent Yield of the Freeze-Thaw-Induced Gelation of Concentrated Aqueous Solutions of the Polymer," Journal of Applied Polymer Science, vol. 77, 1822-1831 (2000).

Lozinsky, V. I. & Damshkaln L. G., "Study of Cryostructuration of Polymer Systems. XVII. Poly(vinyl alcohol) Cryogels: Dynamics of the Cryotropic Gel Formation," Journal of Applied Polymer Science, vol. 77, 2017-2023 (2000).

Mike, C., "FDA Approves Bone Graft," 2002, http://www.news.wisc.edu/view.html?get=7640.

Mongia, N.K., et al, "Mucoadhesive poly(vinyl alcohol) hydrogels produced by freezing/thawing processes: Applications in the development of wound healing systems," J. Biomater. Sci, Polymer Edn, vol. 7, No. 12, pp. 1055-1064 (1996).

Nakane, K., et al., "Properties and Structure of Poly(vinyl alcohol)/Silica Composites," Journal of Applied Polymer Science, vol. 74, 133-138 (1999).

Narasimhan, B. & Peppas, N.A., "Molecular Analysis of Drug Delivery Systems Controlled by Dissolution of the Polymer Carrier," Journal of Pharmaceutical Sciences, vol. 86, No. 3, Mar. 1997.

"New Implants Offer Relief of Spine" 2001, Medical Device and Diagnostic Industry.

Ogata, N., et al., "Poly(vinyl alcohol)-clay and Poly (ethylene oxide)-clay Blends Prepared Using Water as Solvent," Journal of Applied Polymer Science, vol. 66, 573-581 (1997).

Onuki, A. & Puri, S., "Spinodal decomposition in gels," Physical Review E, vol. 59, No. 2, Feb. 1999, R1331-R1334.

Peppas, N.A. & Stauffer, S. R., "Reinforced uncrosslinked poly (vinyl alcohol) gels produced by cyclic freezing-thawing processes: a short review," Journal of Controlled Release, 16 (1991) 305-310.

Stammen, J. A., et al., "Mechanical properties of a novel PVA hydrogel in shear and unconfined compression," Biomaterials, Apr. 22, 2001 (8), 799-806, abstract only.

Stawhecker K.E. & Manias E., "AFM of Poly(vinyl alcohol) Crystals Next to an Inorganic Surface," Macromolecules, 2001, 34, 8475-8482.

Strawhecker, K.E. & Manias, E., "Structure and Properties of Poly(vinyl alcohol)/NA+ Montmorillonite Nanocomposites," Chem. Mater, 2000, 12, 2943-2949.

Takahashi, N., et al, "Effects of cononsolvency on gelation of poly(vinyl alcohol) in mixed solvents of dimethyl sulfoxide and water," Polymer 44 (2003) 4075-4078.

Takeshita, H. et al, "Small-angle neutron scattering studies on network structure of transparent and opaque PVA gels," Physica B 311 (2002) 78-83.

Takeshita, H., et al, "Spinodal Decomposition and Syneresis of PVA Gel," Macromolecules 2001, 34, 7894-7898.

UPMC Surgeons Implanting Metal Cages into the Spine to Treat Chronic Low Back Pain, Neurosurgery News, 1999, University of Pittsburgh.

Willcox, P. J., et al, "Microstructure of Poly(vinyl alcohol) Hydrogels Produced by Freeze/Thaw Cycling," Journal of Polymer Science: Part B: Polymer Physics, vol. 37, 3438-3454 (1999).

Vago, R., "Novel Natural Materials for Bone Substitutes and Hard Tissue Remodeling," http://www.bgu.ac.il/bgn/bone.html.

Yamaura K., et al, "Gels of Syndiotacticity-Rich Poly(vinyl Alcohol)-Water/Dimethyl Sulfoxide or—Water/Ethylene Glycol Solutions," Journal of Applied Polymer Science, vol. 34, 2347-2354 (1987).

Yamaura, K. et al., "Properties of Gels Obtained by Freezing/Thawing of Poly(vinyl Alcohol)/Water/Dimethyl Sulfoxide Solutions," Journal of Applied Polymer Science, vol. 37, 2709-2718 (1989).

Yokoyama, F., et al, "Morphology and structure of highly elastic poly (vinyl alcohol) hydrogel prepared by repeated freezing-and-melting," Colloid & Polymer Sci 264: 595-601 (1986).

Yu, Y, et al, "Preparation and properties of poly (vinyl alcohol) clay nanocomposite materials," Polymer 44 (2003) 3553-3560.

Hong, P, et al, "Solvent Effect on Structural Change of Poly(vinyl alcohol) Physical Gels," Journal of Applied Polymer Science, vol. 69, 2477-2486 (1998).

Bao, Q. & Yuan, H.A, "Prosthetic Disc Replacement: The Future?," Clinical Orthopaedics and Related Research, No. 394, pp. 139-145, 2002.

Bao, Q. et al, "The artificial disc: theory, design and materials," Biomaterials vol. 17, No. 12, (1996) 1157-1167.

Bray, J.C. & Merrill, E. W., "Poly(vinyl Alcohol) Hydrogels. Formation by Electron Beam Irradiation of Aqueous Solutions and Subsequent Crystallization," Journal of Applied Polymer Science, vol. 17, pp. 3779-3794, 1973.

Bray, J.C. & Merrill, E. W., "Poly(vinyl alcohol) Hydrogels for Synthetic Articular Cartilage Material," Biomed. Mater. Res., vol. 7, pp. 431-443 1973.

Diwan, A. D. et al, "Current Concepts in Intervertebral Disk Restoration," Tissue Engineering in Orthopedic Surgery, vol. 31, No. 3, pp. 453-464, Jul. 2000.

Doehring, T.C. et al, "Cyclic Load-Displacement Characteristics of Lumber Functional Spinal Units," $46^{th}$ Annual Meeting, Orthopaedic Research Society, Mar. 12-15, 2000.

Gomes, K. et al, "The Effect of Dehydration History on Associating Hydrogels for Nucleus Pulposus Replacement," Society for Biomaterials, $28^{th}$ Annual Meeting Transactions, 2002.

Griffith, S. L. et al, "A Multicenter Retrospective Study of the Clinical Results of the LINK® SB Charité Intervertebral Prosthesis," Spine, vol. 19, No. 16, 1842-1849, 1994.

Hassan C. M. & Peppas N. A., "Structure and Morphology of Freeze/Thawed PVA Hydrogels," Macromolecule, vol. 33, No. 7, 2472-2479, 2000.

Kawanishi K. et al, "Thermodynamic consideration of the sol-gel transition in polymer solutions," $35^{th}$ Annual Meeting of the Society of Polymer Science, Japan, 1986.

Lozinsky, V. I. et al, Swelling behavior of poly(vinyl alcohol) cryogels employed as matrices for cell immobilization), Enzyme Microb. Technol, vol. 18, 561-569, 1996.

Marolongo, M., et al, "Novel Hydrogel Copolymers for Intervertebral Disc Replacement," Sixth World Biomaterials Congress Transactions, 2000.

Norton, B. K, et al, "Mechanical Evaluation of a Structural Hydrogel for Use as a Spinal Disc Nucleus," Sixth World Biomaterials Congress Transactions, 2000.

Oka, M. et al, "Development of artificial articular cartilage," Proc Instn Mech Engrs vol. 214 Part H, 59-68, 2000.

Peppas, N. A. et al, "Physicochemical Foundations and Structural Design of Hydrogels in Medicine and Biology," Annu. Rev. Biomed. Eng., 02:9-20, 2000.

Takeshita, H. et al, "Gelation Process and Phase Separation of PVA Solutions as Studied by a Light Scattering Technique," Macromolecules 32, 7815-7819, 1999.

Urushizaki, F. et al, "Swelling and mechanical properties of poly(vinyl alcohol) hydrogels," International Journal of Pharmaceutics, 58 135-142, 1990.

Wiesel, S.W. et al, "Industrial Low-Back Pain-A Prospective Evaluation of a Standardized Diagnositc and Treatment Protocol," Spine, vol. 9, No. 2, 199-203, 1984.

Wilke, H-J, et al, "Prosthetic Disc Nucleus Restores the Flexibility and Disc Height of a Disc After Nucleotomy," Sixth World Biomaterials Congress Transactions, 2000.

Zeegers, W. S., et al, "Artificial disc replacement with the modular type SB Charit III: 2-year results in 50 prospectively studied patients," Eur Spine J, 8:210-217, 1999.

Bao, Q.B., & Yuan, H. A., "Nucleus Replacement," Spine, vol. 27, No. 11, 2002, 1245-1247.

Bodugoz-Senturk et al., Biomaterials 29: 141-149 (2008).

Choi et al., Biomaterials 28: 772-780 (2007).

BioCure—Other Product Opportunities for BioCure's PVA Hydrogels.

CryoLife, Inc.—Emerging Products, BioDisc Nucleus Pulposus Replacement.

CryoLife, Inc.—BioGlue Surgical Adhesive.

Biosyntech—BST-Gel Technology.

Biosyntech—Regenerative Medicine Products & Therapeutic Delivery Technologies.

Biosyntech—What is Ultrasan?

Biosyntech—BST-Disc for Restoration of Collapsed or Degenerated Intervertebal Discs.

Disc Dynamics—What is the DASCOR System?

Disc Dynamics—Product Availability.

Disc Dynamics—DASCOR, Christopher Yeung Case Study One.

Gentis Inc.—Medical Technology, DiscCell.

Gentis Inc.—Medical Technology, DiscCell Delivery System.

Loman and Marcolongo's Company Gelifex featured in Philadelphia Business Journal.

Spine Wave, Inc.—NuCore Injectable Nucleus.

Spine Wave Begins Patient Enrollment in NuCore Injectable Nucleus Degenerative Disc Disease Feasibility Study.

Trans1—PDR: Percutaneous Disc Reconstruction.

Trans1—PNR: Percutaneous Nucleus Replacement.

* cited by examiner

SYSTEMS AND METHODS FOR CONTROLLING AND FORMING POLYMER GELS

CROSS REFERENCES TO RELATED APPLICATIONS

The present application claims the benefit of U.S. Provisional Application No. 60/400,899, filed Aug. 2, 2002, the entire contents of the application being incorporated herein by reference in its entirety.

BACKGROUND OF THE INVENTION

Lower back pain affects over 65 million people in the United States with an estimated 12 million of these cases arising from degenerative disk disease. The back is particularly susceptible to damage and disease due to its complex structure. The spine is a complex structure of articulated bone and cartilage comprised of a column of vertebrae separated by vertebral disks (FIG. 1). These vertebral disks act as an intervening cushion to mitigate and distribute loads transferred along the spinal column.

The anisotropic structure of the intervertebral disk efficiently achieves the appropriate mechanical properties required to cushion complex spinal loads. The inner viscoelastic material, termed the nucleus pulposus, occupies 20-40% of the total disk cross-sectional area. The nucleus usually contains between 70-90% water by weight. The nucleus is composed of hydrophilic proteoglycans that attract water into the nucleus and thus generate an osmotic swelling pressure ranging between 0.1-0.3 MPa, which supports the compressive load on the spine. The nucleus is constrained laterally by a highly structured outer collagen layer, termed the annulus fibrosus (FIG. 1). The nucleus pulposus is always in compression, while the annulus fibrosus is always in tension. Although it comprises only one third of the total area of the disk cross-section, the nucleus supports 70% of the total load exerted on the disk. The intervertebral disk becomes less elastic with age, reaching the elasticity of hard rubber in most middle-aged adults as the nucleus loses water content. This water loss will also cause the disk to shrink in size and will compromise its properties.

In degenerative disk disease, the nucleus pulposus can become distorted under stress, resulting in the extrusion of part of the pulposus out through the annulusfibrosus, causing pressure against the surrounding nerves. This process is called herniation. The damage to the disk can often be irreversible if part of the pulposus is lost. The majority of disk injuries occur in the lumbar region, and the most common area of disease occurs at L4/L5 and L5/S1.

A laminectomy (surgical removal of part of a herniated disk—typically the nucleus pulposus) may be performed to relieve pressure on local neural tissue. This approach is clearly a short-term solution, given that the load bearing ability of the nucleus would be reduced with loss of material. Despite this, over 200,000 laminectomies are performed each year, with a success rate of 70-80%.

Arthrodesis or fusion is a more permanent method for surgically treating degenerative disk disease. Fusion is accomplished with or without internal fixation. While internal fixation has become increasingly popular, this technique has its share of complications. Fracture, neurological damage, and osteoporosis have been observed in patients who have undergone internal fixation fusions. The ability of the bone to fuse will vary from patient to patient, with the average likelihood of success ranging from 75-80%. Spinal fusion will cause stiffness and decreased motion of the spine. Additionally, fusion can also put stress on adjacent vertebrae in the spine, which can accelerate disease in adjacent disks and lead to additional back surgery.

A successfully designed artificial disk would replace a worn out disk while protecting patients from incurring problems at an adjacent level of the spine. Several artificial disk prostheses have been proposed in the prior art. Many of these prosthesis attempt complete replacement of the disk, including the nucleus and the annulus fibrosus. Given that the intervertebral disk is a complex joint with multi-directional loading, the design of a prosthesis that mimics the articulation and mechanical behavior of a natural disk is extraordinarily difficult. For example, when the body is supine, compressive loading on the third lumbar disk is 300 N, rising to 700 N in an upright stance, then to 1200 N when bending forward by 20°. Additionally, moments of 6 N-m are often achieved during flexion and extension, with up to 5° of rotation. For adequate safety, a preferred compressive strength of the entire disk is 4 $MN/m^2$.

The most extensive experience to date with a complete disk replacement is that obtained with the SB Charité III prosthesis. This prosthesis has been used extensively in Europe since 1987, and has been implanted into over 3,000 patients. The SB III is designed with a polyethylene spacer placed between two cobalt chromium endplates. Two year follow-up studies have shown good clinical success in patients. Another study concerned a complete disk prosthesis consisting of a polyolefin core reinforced with carbon black, which is attached to two titanium plates. Preliminary results are not promising, since the core fractured in 2 of the implants.

Both of the examples presented above serve to indicate that there is considerable commercial effort being expended in the development of artificial disks. However in both cases the mechanical equivalence of these components to the human intervertebral disks is somewhat doubtful and the long term clinical prognosis is still unclear.

As an alternative to the complete replacement of intervertebral disks, the nucleus pulposus alone can be replaced, leaving the annulus fibrosus intact. This approach is advantageous if the fibrosis is intact, in that it is less invasive, and the annulus can be restored to its natural fiber length and fiber tension. In replacing the nucleus, it is desirable to find a material that is similar in properties to the natural nucleus. Prior art describes bladders filled with air, saline, or a thixotropic gel. To prevent leakage, the membrane material comprising the bladder must be impermeable, which inhibits the natural diffusion of body fluid into the disk cavity, preventing access to necessary nutrients.

To generate a more natural disk replacement material, several research groups have investigated polymeric hydrogels as a possible replacement for the nucleus pulposus. Hydrogels are good analogs for the nucleus pulposus, in that they typically possess good viscoelastic properties and can offer good mechanical behavior. Additionally, they contain a large amount of free water, which permits a prosthesis made from a hydrogel to creep under compression and handle the cyclical loading without loss of elasticity, similar to a natural nucleus pulposus. The water permeability of these materials also allows diffusion of body fluid and nutrients into the disk space. Control of this pore structure, and the consequent control of the nutrient access to all parts of the implant, may be critical for future prosthetic implants.

Others have investigated the use of polyacrylonitrile-polyacrylamide multiblock copolymers encased in a jacket made from ultra high molecular weight polyethylene fibers. These systems absorb up to 80% of their weight in water. Polyvinyl alcohol (PVA) and copolymers of PVA and poly vinyl pyrrolidone (PVP) have produced prostheses with mechanical properties similar to natural disks. These materials have the additional advantage of having clinical success in other medical devices. Gels formed from PVA are usually prepared via a freeze-thaw process or via external crosslinking agents. In addition, hydrogel-based nuclei can contain therapeutic drugs which slowly diffuse out after implantation. Although no clinical data is currently available for these materials, biomechanical testing on cadaver joints has shown similar mechanical properties to natural disks.

SUMMARY OF THE INVENTION

The preferred embodiments of the present invention provide methods of making a gel and controlling a property of the gel. In accordance with a preferred embodiment of the present invention, a method for making a gel includes comprising dissolving a vinyl polymer in a first solvent to form a vinyl polymer solution and introducing the vinyl polymer solution in a volume of a second solvent to cause gelation, the second solvent having a higher Flory interaction parameter at a process temperature than the first solvent. The Flory interaction parameter ($\chi$) is dimensionless and depends on, for example, temperature, concentration and pressure. Solvents can be characterized as having a low $\chi$ value or solvents having a higher $\chi$ value wherein $\chi=0$ corresponds to a solvent which is similar to a monomer. A solvent having a higher $\chi$ value is characterized as a solvent that causes a gelation process at a temperature. Preferably the second solvent used in the preferred embodiment has a Flory interaction parameter in the range of 0.25 to 1.0. Typically, first and second solvent characteristics are chosen to allow use of the method of the preferred embodiment at room temperature or at body temperature of a mammal. The gel produced by the method of the invention has physical cross-linking, and is substantially free of chemical crosslinking agents. In a preferred embodiment, the vinyl polymer is polyvinyl alcohol.

In some embodiments, a plurality of cycles of contacting the vinyl in an immersion solvent (second solvent) and contacting with the first solvent are performed. Alternatively, the method may include subjecting the gel to at least one freeze-thaw cycle. The polyvinyl alcohol (PVA) hydrogels thus may be both a thetagel and a cryogel. Partial gelling can be accomplished with either method and then completed using the other, or even alternating between the two methods.

While the examples and discussion herein are directed towards vinyl polymers and in particular PVA hydrogels, thetagels can be made in a similar manner using any polymer that possesses the appropriate kind of phase diagram as described hereinafter with respect to the Flory interaction parameter. A mechanical force can be applied to the gel during the gelling process, changing the manner in which it gels and alternatively producing oriented gelation.

In several embodiments, the vinyl polymer is highly hydrolyzed polyvinyl alcohol of about 50 kg/mol to about 300 kg/mol molecular weight. In other embodiments, the vinyl polymer is highly hydrolyzed polyvinyl alcohol of about 100 kg/mol molecular weight. The vinyl polymer solution is about 1 weight percent to about 50 weight percent solution of polyvinyl alcohol based on the weight of the solution. Preferably, the vinyl polymer solution is about 10 weight percent to about 20 weight percent solution of polyvinyl alcohol based on the weight of the solution.

The first solvent is selected from the group of solvents having a low $\chi$ value that is not sufficient to enable gelation, i.e., solvents in which the energy of interaction between a polymer element and a solvent molecule adjacent to it exceeds the mean of the energies of interaction between the polymer-polymer and the solvent-solvent pairs, as discussed below. In several embodiments, the first solvent is selected, without limitation, from the group consisting of deionized water, dimethyl sulfoxide, an aqueous solution of a $C_1$ to $C_6$ alcohol and mixtures thereof.

In general, the immersion solution comprises a solvent having a high or sufficient $\chi$ value that enables gelation. In some preferred embodiments, the immersion solution is an aqueous solution of a salt of an alkali metal, typically sodium chloride. In other embodiments, the immersion solution is an aqueous solution of a $C_1$ to $C_6$ alcohol, typically an aqueous solution of an alcohol chosen from the groups consisting of methanol, ethanol, i-propanol, t-propanol, t-butanol and mixtures thereof. In certain embodiments, the immersion solution is an aqueous solution of methanol.

In general, the vinyl polymer gels of the present invention can be made in-situ for applications such as filters, microfluidic devices or drug release structures in situations in which freeze-thaw gelation may be difficult or impossible to execute.

In one embodiment, the vinyl polymer solution is placed in a chamber having at least two sides and a membrane. The membrane has properties that contain the vinyl polymer while providing access to small molecules and solvents.

In some embodiments, the vinyl polymer solution is separated by the membrane from at least two different immersion solvents, typically a first immersion solvent and a second immersion solvent. In some embodiments, the first immersion solvent is an aqueous solution of sodium chloride from about 1.5 molar to about 6.0 molar. In some embodiments, the second immersion solvent is an aqueous solution of sodium chloride from about 2.0 molar to about 6.0 molar. In other embodiments, the first immersion solvent is a 1.5 molar aqueous solution of sodium chloride and the second immersion solvent is an aqueous solution of sodium chloride from about 2.0 molar to about 6.0 molar. In such embodiments, a gradient in chemical potential is formed across the vinyl polymer solution between at least two different immersion solvents. In one embodiment, a gradient in chemical potential is formed across the vinyl polymer solution of about 4 mol.cm$^{-1}$.

In general, a gradient of a property is formed across the vinyl polymer gel that corresponds to the gradient in chemical potential formed across the vinyl polymer solution. Typically, the property is at least one of light transmission, gravimetric swell ratio, shear modulus, load modulus, loss modulus, storage modulus, dynamic modulus, compressive modulus, cross-linking and pore size.

In some embodiments, one or both immersion solvents are changed in a temporal pattern to modulate the spatial gradient of a physical property. Such temporal cycling is done on a time scale shorter than the diffusion time to make an inhomogeneous gel. In this way, gels can be produced with a similar set of properties on the edges or peripheral region and another set of properties in the central region, such as greater cross-linking in the peripheral region as compared with the central region. Temporal cycling of immersion solvents can also be used to modify the structure of the gel, for example, pore size, for production of filters. In such filters, small, locally varying pore size may be useful for some forms of chromatography (through size exclusion) or any other filtering application that requires pore size control.

Additional compounds can be combined in the physically cross-linked gel, including but not limited to, ionic or nonionic species such as hyaluronic acid, polyacrylic acid and therapeutic agents.

In one embodiment, the invention provides a physically cross-linked hydrogel comprising at least about 10 weight percent poly(vinyl alcohol) solution gelled by immersion in about 2 to about 3 molar sodium chloride wherein the hydrogel is about 14 percent to about 21 percent physically cross-linked. In such an embodiment the final gel comprises about 12 to about 29 percent poly(vinyl alcohol).

The preferred embodiments of the present invention also provide articles of manufacture comprising a vinyl polymer gel having at least one gradient of mechanical properties. PVA thetagels may be used as a biocompatible load bearing or non-load bearing material for replacement, repair or enhancement of tissue. In general, PVA thetagels can replace PVA cryogels in applications where PVA cryogels are used. A thetagel, in accordance with the present invention, is formed by using a second solvent as defined hereinbefore as having a Flory interaction parameter that is sufficient to cause gelation.

In one embodiment, a one-piece prosthetic intervertebral disk is made comprising a polyvinyl polymer hydrogel wherein the distribution of mechanical properties of the one-piece prosthetic intervertebral disk approximates the spatial distribution of the mechanical properties of the combination of the nucleus pulposus and the annulus fibrosis of the natural intervertebral disk.

High compression PVA thetagels can be made by placing PVA in a reverse osmosis membrane with NaCl and then making the outside concentration of NaCl quite high to compress PVA/NaCl. The NaCl concentration will climb as water leaves the reverse osmosis membrane gelling the PVA at high pressure. The concentration of PVA can be modified by the ratio of NaCl to PVA inside the reverse osmosis membrane.

In a preferred embodiment, gel microparticles can be made through gelation during agitation or by dropping blobs of fluid into a crosslinking solvent, such as the immersion solution.

In a preferred embodiment, gels can be embedded with particles that degrade (or do not adsorb) to "imprint" a pattern ("empty spaces") on the gel or as the drug release centers. Embedding neutrally charged polymers of varying molecular weights can be used to "space fill" the gel. These polymers are removable after the process, leaving a controlled pore structure. Materials that are sensitive to freeze-thaw cycles can be encapsulated. The gels can be embedded with particles or polymers that are electrostatically charged to provide extra repulsion at high compressions but are collapsed in high salt. Such embedded particles can be those that are active in some manner (e.g. for catalyses). Hydroxyapatite particles or other osteoinductive particles, agents, and similar moieties can be embedded to encourage bony ingrowth for possible cartilage replacement.

In a preferred embodiment, poly(vinyl alcohol) gels can be used to contain and release bio-active compounds such as growth factors, fibronectin, collagen, vinculin, chemokin and cartilage including therapeutic agents. The teachings with respect to incorporation of therapeutic agents of U.S. Pat. Nos. 5,260,066 and 5,288,503 are herein incorporated in their entirety. Contained compounds such as therapeutic agents or drugs can be released over time to modulate the local growth of normal tissues such as bone, blood vessels and nerves or tumors.

Temporal modulation of immersion solvents can produce thetagels in accordance with the preferred embodiment with appropriate structure and physical properties for containing and releasing drugs and other bioactive molecules. In one embodiment, an outer skin is formed that is highly crosslinked and an inner layer containing the drug/active agent is only weakly crosslinked. In such an embodiment, the outer skin is the rate limiting component and has a constant release rate. Thus, drug release in accordance with a preferred embodiment includes the release profile that is tunable by controlling the spatial gradient in PVA crosslinking.

In a preferred embodiment, the gel can be formed in-situ for applications such as filters, microfluidics or drug release where freeze-thaw might be difficult or impossible to execute.

In one embodiment, the present invention provides a method of controllably modulating the mechanical properties and structure of hydrogels. In a preferred embodiment, the present invention provides articles of manufacture with one or more gradients of mechanical properties that more closely match the existing gradients of such properties in natural structures. In one embodiment the invention provides prosthetic hydrogel articles of manufacture that mimic the mechanical behavior of natural structures. In a preferred embodiment, the invention provides polyvinyl alcohol prosthetic intervertebral disks that mimic gradients of mechanical properties found in the natural intervertebral disks. In another preferred embodiment, the invention provides a one-piece prosthetic intervertebral disk that mimics the spatial distribution of the mechanical properties of the nucleus pulposus plus annulus fibrosis of the natural intervertebral disk.

In a preferred embodiment, particulates may also be added to the gel. As described hereinbefore, particulates can be added to create a controlled pore structure. Further, in accordance with another preferred embodiment, particulates can be added to provide a particular nanostructured gel. The particles can be either charged or uncharged and allow PVA crystals to nucleate at the surface of the particles. Particles that can be added include, but are not limited to, inorganic or organic colloidal species such as, for example, silica, clay, hydroxyapatite, titanium dioxide or polyhedral oligomeric silsesquioxane (POSS).

In accordance with another preferred embodiment, particles are added to provide a charge effect to change the compressive modulus of the gel, and preferably increase the compressive modulus. This embodiment can use a thetagel having added particles. Upon compressing the gel in a salt solution, a structure having particles with close packing while shielding their charges results. Upon rehydrating with, for example, deionized (DI) water, the charge fields expand and results in a gel in tension. This allows the gel to approximate physical properties of cartilage, for example, at high charged particulate loads.

In accordance with another preferred embodiment, particulates are added to the gel structure to provide mechanical properties such as, for example, wear resistance. The addition of hardened glass (silica) or different clays can provide wear resistance to the gels.

In accordance with another preferred embodiment of the present invention, a method for making a gel and controlling a property of the gel includes forming a thetagel as described hereinbefore by using a first solvent to form a vinyl polymer solution and subsequently introducing a volume of a second solvent to cause gelation, followed by promoting dehydration to controllably structure the gel. This method results in uniformly structuring the gel and homogenizing the physical crosslinking of the PVA thetagel. This structure can be achieved by immersing the contained PVA solution into a solvent which has a Flory interaction parameter that is higher than the theta point for the PVA solvent pair, and subsequently immersing the contained PVA in another solvent having a Flory interaction parameter lower than the theta point for the PVA solvent pair. The process can continue with successive decreases in the Flory interaction parameter until the desired interaction parameter value for the gel is reached.

In another method in accordance with a preferred embodiment of the present invention, the PVA solution can be subjected to a gradually changing solvent quality through a similar range of electrolyte concentrations by the gradual addition of a concentrated NaCl solution to deionized water such that the change of the salt concentration is slower, or equal, to the diffusion process of the gel.

In accordance with another preferred embodiment of the present invention, the PVA solution may be subjected to at least one freeze-thaw cycle to fix the gel into a particular shape and then be immersed in a series of solutions with successively higher Flory interaction parameters until the final desired Flory parameter is reached. Alternatively, the PVA solution is subjected to the one or more freeze-thaw cycles after being immersed in a solution of 2 M NaCl.

In one preferred embodiment, nanoparticles are dispersed into solutions of PVA. The solvent may be water, dimethyl sulfoxide (DMSO), methanol or any other solution that exhibits a Flory interaction parameter that is lower than the theta point for the PVA solvent pair during solution preparation. The PVA/nanoparticle mixture is then subjected to at least one freeze-thaw cycle. Subsequent to the freeze-thaw cycling, the gelled PVA is immersed in a solvent that has a Flory interaction parameter near or higher than the theta point for the PVA/solvent pair to induce further physical crosslinking of the PVA/nanoparticle mixture.

The foregoing and other features and advantages of the systems and methods for controlling and forming polymer gels will be apparent from the following more particular description of preferred embodiments of the system and method as illustrated in the accompanying drawings in which like reference characters refer to the same parts throughout the different views. The drawings are not necessarily to scale, emphasis instead being placed upon illustrating the principles of the invention.

DETAILED DESCRIPTION OF PREFERRED EMBODIMENTS

Figure 1A:
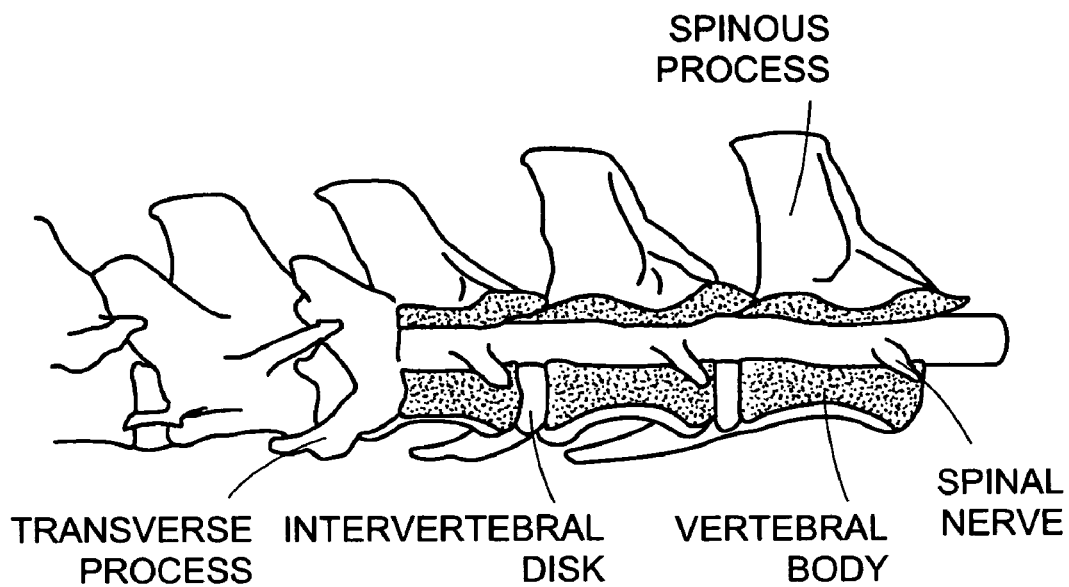
FIGS. 1A and 1B are a diagrammatic representation of spinal anatomy showing transverse process, spinous process and vertebral body of the vertebral bones, the spinal cord and spinal nerves, and the nucleus pulposus of the intervertebral disks. The annulus fibrosis of the intervertebral disk surrounds the nucleus pulposus on lateral, anterior and posterior sides.
Figure 1B:
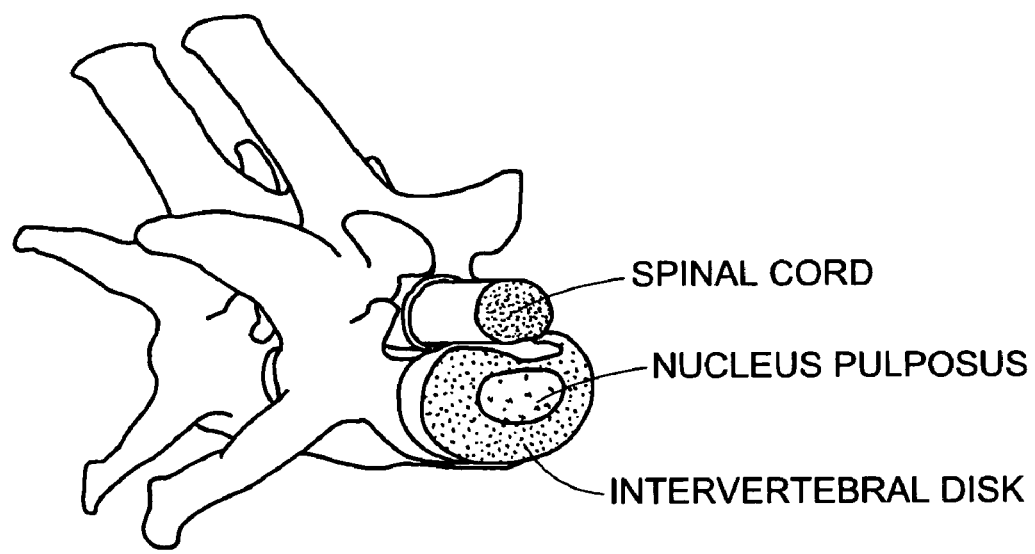

Uniform PVA hydrogels can be generated without chemical crosslinkers, irradiation or thermal cycling to produce a biocompatible material suitable for use as a intervertebral disk prosthesis. Further, a preferred embodiment includes a method used to create the PVA gels that result in a new class of PVA hydrogels which can be designed for specific applications to have a potentially large range of mechanical properties, being controllable, and can be engineered with gradients in structure and physical properties.

As used herein, theta solvent is a solvent that yields, at the theta temperature, solutions of a polymer in the theta state. Theta solvents may be composed of a single solvent or mixture of two solvents, a mixture of a solvent and a nonsolvent, or even a mixture of two nonsolvents in the case of co-solvency as described by Elias, H. G., "Theta Solvents," in Brandrup, J. and E. H. Immergut, Polymer Handbook 3$^{rd}$ Ed., John Wiley and Sons, New York, 1989, the teachings of which are herein incorporated by reference in their entirety.

While not being held to a particular theory, it is thought that forcing poly(vinyl alcohol) polymer chains in solution into close proximity using a theta solvent through a spinodal decomposition mechanism, results in the formation of a physical association that is resistant to dissolution. The methodology utilized in the present invention generates a PVA hydrogel employing the controlled use of solvents having a $\chi$ value sufficient to cause gelation to force the PVA chains to physically associate. To prevent random "crashing out" of the PVA, it is critical that the solvent quality is controlled carefully, and, in particular for larger components, that the solvent "front" enters the PVA solution in a controlled manner. For example, NaCl/deionized (DI) water and methanol/deionized water solutions at temperatures and concentrations in the neighborhood of their "theta" value for PVA were used to force the physical association and subsequent gelling of the PVA. Gels formed in this way are called "thetagels" herein.

The methods are applicable to the creation of materials for use in medical, biological and industrial areas including the controlled delivery of agents (which may include proteins, peptides, polysaccharides, genes, DNA, antisense to DNA, ribozymes, hormones, growth factors, a wide range of drugs, imaging agents for CAT, SPECT, x-ray, fluoroscopy, PET, MRI and ultrasound), generation of load bearing implants for hip, spine, knee, elbow, shoulder, wrist, hand, ankle, foot and jaw, generation of a variety of other medical implants and devices (which may include active bandages, trans-epithelial drug delivery devices, sponges, anti-adhesion materials, artificial vitreous humor, contact lens, breast implants, stents and artificial cartilage that is not load bearing (i.e., ear and nose)), any application where gradients (single or multiple) in mechanical properties or structure are required.

In general, a physically cross-linked poly(vinyl alcohol) gel is prepared from an aqueous poly(vinyl alcohol) solution (from 1% to 50% PVA by weight of the solution) that is gelled by contacting with a solvent having a $\chi$ value sufficient for gelation, hereinafter called the second solvent at a concentration approximating the "theta" concentration for the poly (vinyl alcohol) solution.

The present invention provides a method of producing poly(vinyl alcohol) hydrogels that does not use chemical cross-linkers, irradiation or thermal cycling. The key to the method is controlling the solvent quality, and in particular the diffusion of the second solvent (NaCl or methanol) into a PVA solution to produce a homogenous, physically crosslinked structure.

The present method uses a controlled change in solvents differing in solvent quality, conveniently expressed by the Flory interaction parameter to force the PVA to associate. Because no chemical cross-linkers are used, the gel is substantially free of chemical crosslinkers and thus likely to be as biocompatible as thermally-cycled PVA cryogels. Any residue of NaCl in the gel following equilibration in deionized water is likely to be benign, as its concentration will certainly be below physiologically relevant values.

Figure 2:
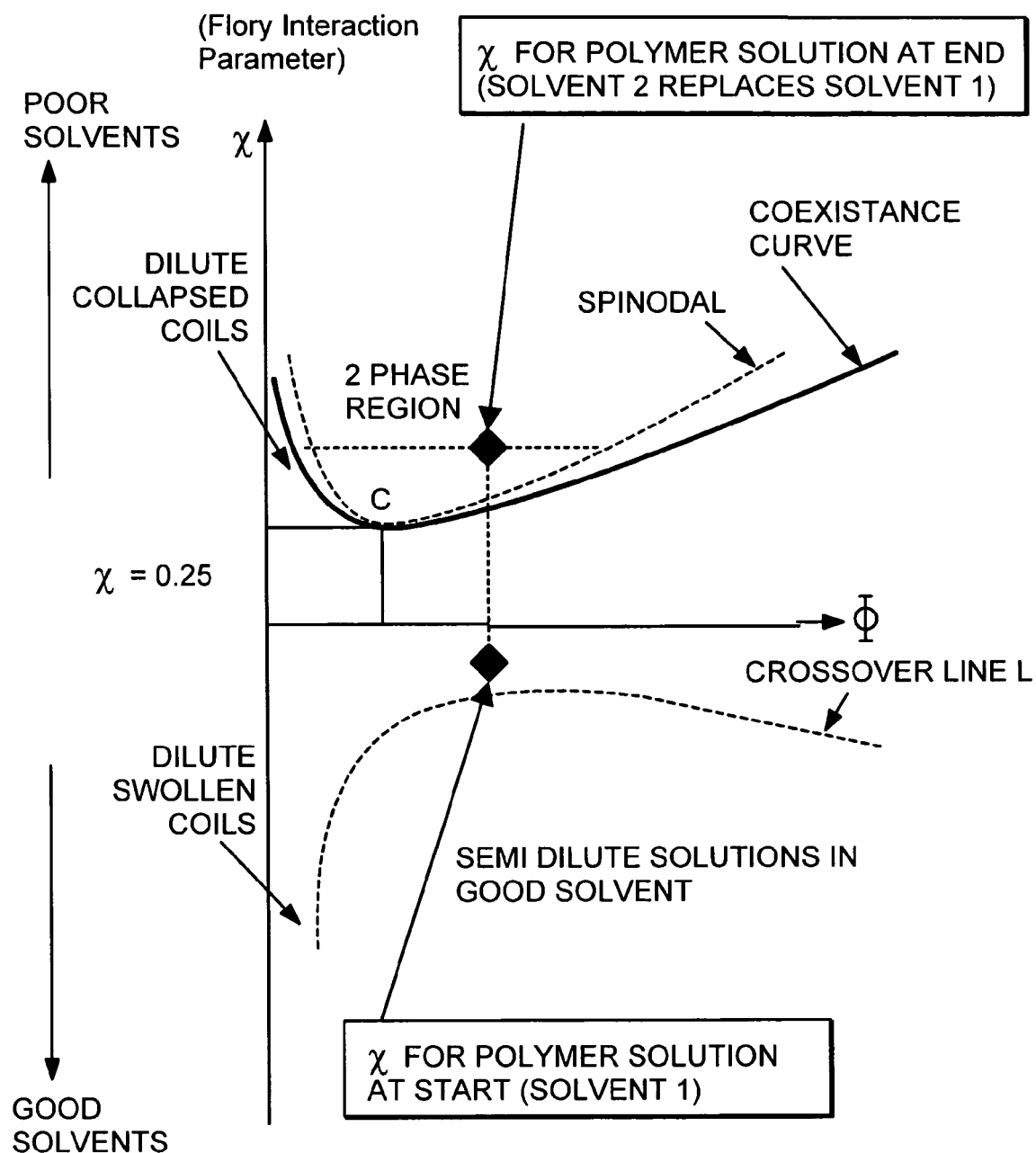
FIG. 2 is a graphical representation of the relationship of the Flory interaction parameter, $\chi$, to the concentration ($\Phi$) of a polymer at a given temperature in accordance with preferred embodiments of the present invention. The abscissa, at $\chi=0.25$, separates polymer solutions in first solvents (below) and polymer solutions in second solvents (above). The arrows and diamonds indicate the effect on $\chi$ produced by replacing solvent 1 with solvent 2.

FIG. 2 illustrates the relationship between the first solvent and the second solvent in terms of the Flory interaction parameter, $\chi$. FIG. 2 is a graphical representation of the relationship of the Flory interaction parameter, $\chi$, to the concentration ($\Phi$) of a polymer at a given temperature. The abscissa, at $\chi$=0.25, separates polymer solutions in first solvents (below) and polymer solutions in second solvents (above) sufficient to cause gelation. The arrows and diamonds indicate the effect on $\chi$ produced by replacing solvent 1 with solvent 2.

In preferred embodiments, $\chi$ of the second solvent must be more positive than the $\chi$ of the first solvent (dissolved PVA solvent) and will preferably be in the range of 0.25 to 2.0. Preferably $\chi$ of the first solvent is in the range of 0.0 to 0.5. In general, the temperature during processing may vary from just above the freezing point of the PVA solution to the melting point of the physical crosslinks formed in the process. The preferable range is from about 0 degrees Celsius to about 40 degrees Celsius. Note that $\chi$ is coupled to temperature and concentration. In preferred embodiments the temporal and spatial change in $\chi$ of the PVA solution (the first solvent) is controlled by contact with another miscible solution (comprising the second solvent), wherein the second solvent modifies the first.

The removal of the need for chemical crosslinkers and radiation processing allows a greater variety of embedded components. For instance many bioactive materials are highly intolerant of chemical crosslinkers and radiation. In addition although in general the freeze-thaw process is gentle on bioactive components there can certainly be envisaged polymers, biopolymers or cells that either cannot be frozen, or act as antifreeze hence preventing the freezing.

The method used to create these thetagels is likely to produce a wider range of material properties and greater control over the physical structure of the final gel than is possible with competing cryogels. The advantage of thetagels over thermally cycled PVA gels for certain applications is outlined below.

Cryogels have a fairly low resolution with regard to their final properties because each thermal cycle produces a dramatic change in the material properties of the gel. The thetagels produced demonstrate that the concentration of the solvent produces a monotonic decrease in swelling ratio once the theta value is passed (See FIG. 7). It is desirable that the ultimate crosslink density is adjustable in proportion to the resolution achievable in the solvent concentration. For example, for the 10% PVA solution immersed in NaCl, the weight percentage of PVA in the final gel varies at a rate of about 7%/mole NaCl.

The preferred embodiments of the present invention provides gels having a starting weight (based on the weight of the solution) from about 1 weight % to about 50 weight % PVA. In preferred embodiments, the weight percent ranges from about 12% to about 29% PVA in the final gel where the immersion solution used was about 2.0 about 3.0 M NaCl (aq). This range of final PVA weight percentages is comparable to that which can be achieved by thermally cycled PVA. With higher NaCl solutions (in excess of 6.0 M) percent PVA of the final gel increases monotonically with NaCl concentration. It has been found that PVA thetagels can be made that exhibit a smooth gradient in spatial properties. In contrast, gradients of properties cannot easily be manufactured in cryogels. Instead, the usual approach is to generate an array of stacked lamellae independently that must be joined in dissolved PVA and then cycled again. Sharp differences in modulus in such an array would create a material with undesirable mechanical properties and with inhomogeneous interfaces. In preferred embodiments, PVA thetagels having a smooth gradient in mechanical properties, can be used to make a prosthetic intervebral disk a central lower modulus "pulposus" having adequate compressive strength and a higher modulus peripheral "annulus" that minimizes creep and undesirable distortion.

Modulus enhancement can be accomplished by incorporation of ionic species. For thetagels produced in NaCl, it is possible to include natural (hyaluronic acid) or synthetic (PAA) polymers to create gels with strain variable compressive moduli. Gelling a PVA/PAA solution in strong NaCl shield the ionizable charges in the PAA while the PVA is crosslinked around the collapsed PAA. Re-equilibration in deionized water will allow expansion of the PAA and pre-stress the PVA matrix. The resulting construct should have a very different mechanical compressive modulus due to the repulsion of the fixed charges on the incorporated PAA.

It is known in the art that PVA elicits little or no host biological response when implanted in animals. For this reason, PVAs are used in a variety of biomedical applications including drug delivery, cell encapsulation, artificial tears, artificial vitreous humor, contact lenses, and more recently as nerve cuffs. However, PVA has generally not been considered for use as a load bearing biomaterial primarily because of its low modulus and poor wear characteristics. The loads that any vertebral implant must withstand will be reasonably high (on the order of 4 MPa in compression) requiring a high compressive modulus. In vivo, the compressive axial load on the intervertebral disk is transferred by the nucleus pulposus to a tensile circumferential load in the annulus fibrosis. Any biomaterial intended to replace the function of an intervertebral disk in its entirety must incorporate similar anisotropic properties.

To improve overall strength, PVA modulus and wear characteristics can be enhanced by the formation of either chemical or physical cross-links. Cross-linking PVA by the addition of chemical agents (such as polyaldehydes), through irradiation, or by freeze-thaw cycling, has been shown to improve the durability of PVA gels. However, chemical additives can leave unwanted residual reactive species behind that make the final product unsuitable for transplant, while irradiation may adversely affect any bioactive material encapsulated in the matrix. Thus, the generation of extensive physical cross-links through freeze-thaw cycling has substantially improved the durability of PVA without the negative side effects produced by chemical or irradiation induced crosslinking. Recent investigations suggest that the physical crosslinks produced by freeze-thaw cycling might generate biomaterials with moduli suitable for use as biocompatible replacements for load bearing structures such as articular cartilage or intervertebral disk.

Solvation of polymers and the "theta" point

Polymers in solution are complex molecules in perpetual dynamic motion. The configuration of an ideal polymer chain is usually described as a "random walk", where the molecule is assumed for simplicity to be freely jointed and free to move where it will. This behavior results in the polymer assuming a spherical shape with a Gaussian distribution. In reality the chain has a number of forces acting on it to define its shape and behavior. In free solution the chain is subject to random motion from Brownian fluctuations arising out of the temperature of the system. At the same time there is a force arising out of how the chain interacts with itself (since it is a long, extended molecule) and its surroundings.

If the polymer is easily solvated by the solution (i.e., it is in a first solvent not having a $\chi$ value sufficient for gelation) it swells as it tries to maximize the amount of polymer chain that is exposed to the solvent. In the first solvent, the energy of interaction between a polymer element and a solvent molecule adjacent to it exceeds the mean of the energies of interaction between the polymer-polymer and solvent-solvent pairs as described by Flory, P. J. in, Principles of Polymer Chemistry, page 424, Cornell University Press, 1953, the teaching of which are herein incorporated by reference in their entirety. The chain is now in a perturbed state and resists contact with neighboring chains and equally resists mechanical compression and deformation. As the solvency changes, this swollen configuration collapses as the quality of the solvent falls.

At the theta point, the solvent quality is such that the random Brownian motions are enough to keep the chain in an ideal, Gaussian distribution. Below this critical threshold the chain segments prefer to be next to each rather than to a solvent molecule, and the chain shrinks (i.e. a second solvent having a $\chi$ value sufficient for gelation). The Flory interaction parameter, $\chi$ is dimensionless, and depends on temperature, pressure, etc. The first solvents have a low $\chi$, while the second solvents have a high $\chi$, with a transition at about $\chi=0.5$. The case $\chi=0$ corresponds to a solvent which is very similar to a monomer. In a lattice model this is the case where the free energy comes entirely from the entropy associated with various chain patterns on the lattice. In such a case, temperature has no effect on structure, and the solvent is said to be "athermal." Athermal solvents are a particularly simple example of good solvents. In most cases the parameter $\chi$ is positive as described by de Gennes, P. G. in, Scaling Concepts in Polymer Physics, First ed. p. 72: Cornell University Press (1979). If the solvent quality is poor enough, the chain will completely precipitate out of solution. This effect can also be obtained by manipulation of the temperature of the solution.

Once the concentration of the polymer solution is high enough, adjustment of the solvent quality can be achieved by replacing at least part of a first solvent with a second solvent that forces inter-chain interaction as well as intra-chain interaction. Once the physical crosslinking has occurred, the later presence of a good solvent, which naturally swells the free polymer, is balanced by the physical crosslinking. With interchain associations the polymer chains are now constrained at certain pinning-points. Consequently as the polymer is solvated, and stretches, it becomes more deformed and is forced into tension. It is the competition between the solvation of the polymer chains and this tension in the deformed chains that give gels their interesting mechanical behaviors. In addition, under certain conditions the polymer chains can be ionized, consequently generating a charge. Adjacent like charges will result in further swelling due to electrostatic repulsion. This is part of the mechanism that gives natural cartilage (collagen and glycosaminoglycans) its high modulus, and high hygroscopic properties.

Gelation mechanism in PVA

Freeze-thaw cycling of solutions of PVA polymer results in the formation of physical cross-links (i.e. weak bonding through an "association" of the polymer chains). PVA hydrogels formed in this manner are termed "cryogels" and are described, for example, in U.S. Pat. Nos. 6,231,605 and 6,268,405, the teachings of which are incorporated herein by reference in their entirety. Importantly, the techniques utilized to create PVA cryogels do not require the introduction of chemical crosslinking agents or radiation. Cryogels are therefore easily produced with low impact on incorporated bioactive molecules. However, incorporated molecules are limited to those that can tolerate the freeze-thaw cycles required to make the gel. Thus the resulting material can contain bioactive components that will function separately following implantation. PVA cryogels are also highly biocompatible (as will be the proposed PVA "thetagels" to be presented later). They exhibit very low toxicity (at least partially due to their low surface energy), contain few impurities and their water content can be made commensurate to tissue at 80 to 90 wt %.

There is still some debate over the exact mechanism that drives the gelation of PVA through a freeze-thaw cycle. However, three models have been proposed to explain the physical crosslinking that occurs during the freeze-thaw cycle: 1) direct hydrogen bonding; 2) direct crystallite formation; and 3) liquid-liquid phase separation followed by a gelation mechanism. The first two steps suggest that the gel forms through a nucleation and growth (NG) phase separation, whereas the third option pictures the process as a spinodal decomposition (SD) phase separation. Hydrogen bonding will form nodes and crystallite formation will form larger polymer crystals. However both of these mechanisms will form closely connected crosslinks, with relatively small crosslinking nodes. This observation is supported by studies on the gelation mechanism of PVA. Spinodal decomposition on the other hand causes redistribution of the polymer into polymer rich and polymer poor regions followed by a gelation process which results in more distantly spaced crosslinks. It is thought that phase separation through spinodal decomposition is likely to be responsible for the improved mechanical properties of PVA after crosslinking and occurs due to a quenching of the polymer solution. During the freezing process, the system undergoes a spinodal decomposition whereby polymer rich and poor phases appear spontaneously in the homogeneous solution. This process occurs because the phase diagram of quenched PVA (and polymers in general) at certain temperatures can have two coexisting concentration phases. The polymer rich phases are therefore highly concentrated which enhances the natural (weak) gelation of the PVA.

For cryogels, the physical characteristics depend on the molecular weight of the uncrosslinked polymer, the concentration of the aqueous solution, temperature and time of freezing and the number of freeze-thaw cycles. Thus the properties of a cryogel can be modulated. However, since the material's properties change dramatically at every freeze-thaw step, control over the properties of the finished gel is somewhat limited. The thetagels described broaden the range of functionality currently provided by PVA cryogels.

In general, the modulus of the PVA cryogel increases with the number of freeze-thaw cycles. In one experimental series, thermally cycled PVA cryogels had compressive moduli in the range of 1-18 MPa and shear moduli in the range of 0.1-0.4 MPa. Stammen, J. A., et al., Mechanical properties of a novel PVA hydrogel in shear and unconfined compression Biomaterials, 2001 22: p. 799-806.

As cryogels are crosslinked by physical and not chemical means, there is some concern about their structural stability. The modulus of PVA in aqueous solution increases with soak time in distilled water at constant temperature. In one experiment, conducted over 40 days, the modulus increased by 50%. Putatively, during aqueous aging, the increase in strength, with the concomitant loss of soluble PVA, is the result of an increase in the order of the supramolecular packing of the polymer chains. There are significant implications in this data for the long-term storage effects of the freeze-thaw gelled PVA.

It is also important to understand the effects of loss of polymer over time and how that impacts the local host biological environment. It should be noted that in this example, the cryogel was only freeze-thaw cycled once, although others have shown PVA dissolution following multiple freeze-thaw cycles. In general, there is very little information about the stability of PVA cryogel modulus under repeated load cycling (fatigue).

As might be expected, the swelling of PVA cryogels at any time point decreases with increasing number of freeze-thaw cycles, indicating a densification of the PVA gel, most likely due to a higher crosslink density. In the long term, following gelation and under static conditions, the ultimate swelling ratio decreases while the modulus increases with time.

In freeze-thaw processing, temperature is used to force a phase separation of the PVA solution, thus enhancing the gelation mechanism in the PVA (it should be noted that even at room temperature a solution of PVA begins to gel weakly over time).

Solvent quality is related to both temperature and the chemical interaction of the solvent to the polymer, and is conveniently described by the Flory interaction parameter $\chi$. In a preferred embodiment, the manipulation of the solvent quality through some process other than temperature allows much greater control over the gelation process while permitting the method to be practiced at approximately room temperature. In particular, by using aqueous based solvents for PVA, the system can be chosen to minimize impact on materials embedded in the PVA, and can allow fine spatial and temporal control over the final structure of the gel. In a particular solvent, the critical parameter defining the transition from the first to second solvent (and hence driving the phase separation) is known as the theta temperature. An example list is presented in Table 1 below.

TABLE 1

Theta temperatures for PVA in various solvents
(from Brandrup, J. and E. H. Immergut, Polymer
Handbook. Third ed. 1989, New York: John Wiley & Sons.).

| Solvent | Volume Ratio | Theta Temperature [° C.] |
|---|---|---|
| t-Butanol/Water | 32:68 | 25 |
| Ethanol/Water | 41.5:58.5 | 25 |
| Methanol/Water | 41.7:58.5 | 25 |
| i-Propanol/Water | 39.4:60.6 | 25 |
| n-Propanol/Water | 35.1:64.9 | 25 |
| NaCl/Water | 2 Moles/L | 25 |
| Water | — | 97 |

Physically cross-linked PVA gels may also be produced through thermal cycling (not necessarily with freezing) combined with dehydration. Such gels are potentially suitable for use in load bearing applications (i.e. artificial articular cartilage). Examination of the material properties of this thermally cycled PVA found that the material distributes stress more homogeneously than stiff single-phase biomaterials (ultra-high molecular weight polyethylene (UHMWPE)) and preserves the lubrication film gap readily in simulated articular cartilage loading. The material sustained and distributed pressure in the thin film of between 1 and 1.5 MPa. In transient load tests, the PVA withstood and distributed loads of nearly 5 MPa.

Studies have been conducted that further examined the wear properties of their thermally cycled, dehydrated PVA under a variety of conditions. The wear rate found in unidirectional pin-on-disk (against alumina) experiments was comparable to that of UHMWPE (although this test is probably not the most suitable to perform for biological implants). However, in reciprocating tests, the wear rate was up to 18 times larger. To improve the wear properties, PVA of higher molecular weight and additionally crosslinked by gamma-radiation (doses over 50 kGy) was tested. Such treatment reduced the wear rate considerably (to about 7 times that of UHMWPE). However, in both radiation and thermally crosslinked PVA the wear rate does not appear adequate for applications where the opposing surface has high hardness. Additionally, irradiation would adversely affect bioactive materials loaded into the gel.

Methods in accordance with a preferred embodiment include the following:

PVA solutions. To make the 10% solution, 20 grams of PVA (100 kg/mole; 99.3+% hydrolyzed; JT Baker) was dissolved in 180 grams of deionized water at 90° C. for one to two hours. To make the 20% solution, 30 grams of PVA was dissolved in 180 grams of deionized water, the solution was stirred continuously until 60 grams of water evaporated to generate a final solution of 20% PVA.

PVA gelation. 4-5 ml of PVA solution of 10 or 20 weight percent were injected into pre-wetted Slide-A-Lyzer Dialysis cassettes (Pierce, Rockford, Ill.) with a molecular weight cutoff of 3500 Daltons. The 10% PVA solutions were then immersed in NaCl aqueous solutions of 1.5 M, 2.0 M, 2.5 M or 3 M. The 20% PVA solution was immersed in 3.0M NaCl. To demonstrate that the gelation effect was not NaCl/aqueous solvent-dependent, a 10% PVA solution in a dialyzer cassette was immersed in a 50/50 methanol/water solution. After 3 days, all of the cassettes containing 10% PVA solution were removed from their respective solvents. The gels were then removed from the cassettes and placed in DI water for at least 5 days to allow initial PVA crystal dissolution the cassette containing the 20% PVA solution was removed after 3 days. The PVA gel was removed from the cassette and a portion was stored in DI water. The remaining PVA gel was returned to the 3M NaCl solution. At 6 and 12 days, portions of the 20% PVA gel were removed and placed into DI water for at least five days before further testing.

Quantitative Characterization

To quantify the effect on the structure of the gels of immersion solution molarity and time immersed, differential scanning calorimetry (DSC), gravimetric swell ratio analysis and dynamic mechanical analysis (DMA) were performed on the samples.

Differential Scanning Calorimetry. DSC thermograms were obtained using an instrument, for example, a TA Instruments Q1000 (TA Instruments, New Castle, Del.). Selected wet PVA gel samples between 5 and 15 mg were removed from deionized water storage after 5 days, blotted dry and crimped into alodized-aluminum hermetic pans. Scans were performed at 5° C./min from 5° C. to 120° C. The total enthalpy change for the melting of the gel physical crosslinks was estimated using a linear integration from the departure from baseline (typically near 40° C.) to return to baseline (typically near 90° C.). Following DSC analysis, the hermetic pans were punctured, weighed and placed in a vacuum oven for dehydration. After two days of dehydration the pans were reweighed to determine the percent PVA in the original sample.

Gravimetric swell ratio. Samples of PVA gel from each sample were removed from deionized water storage after 5 days, blotted with a tissue and dehydrated in a vacuum oven for 2 days. The gravimetric swell ratio was calculated as the ratio of the mass of water in the gel to the mass of PVA in the gel.

Dynamic Mechanical Analysis. To examine the effect of curing solvent quality, dynamic mechanical analysis was performed using a Perkin-Elmer TMA 7 (Perkin Elmer, N.J.) on the 10% PVA 3 M NaCl and, 2 M NaCl samples. To examine the effect of aging in the curing solvent, DMA was also performed on the 20% 3 M NaCl 3 day and 12 day samples. Samples were cut into rectangles and tested in unconfined compression with a static load of 250 mN (10% samples) or 1000 mN (20% samples). The storage (and loss moduli for the 10% samples) were determined for a frequency sweep from 1 to 2 Hz at room temperature.

In a preferred embodiment, forcing poly(vinyl alcohol) polymer chains in solution into close proximity (through a spinodal decomposition mechanism) results in the formation of a physical association that is resistant to dissolution. This methodology generates a PVA hydrogel employs the controlled use of the second solvents having a $\chi$ value sufficient to cause gelation to force the PVA chains to physically associate. It is critical that the solvent quality is controlled carefully, and in particular for larger components, that the solvent "front" enters the PVA solution in a controlled manner. NaCl/deionized water and methanol/deionized water solutions at concentrations in the neighborhood of their "theta" value for PVA were used to force the physical association and subsequent gelling of the PVA. Gels formed in this way are termed "thetagels".

Figure 3:
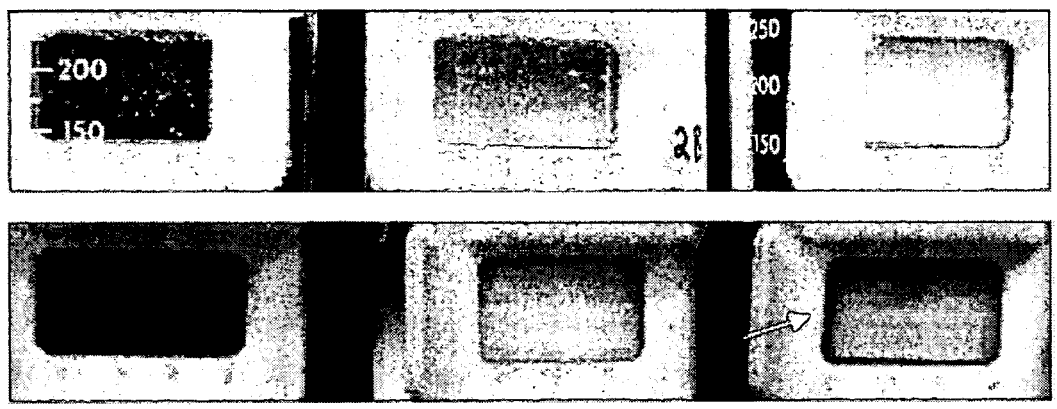
FIG. 3 shows 10% PVA solution in dialyzer cassettes after 1 day (top) and 3 days (bottom) of immersion in curing solution in accordance with a preferred embodiment of the present invention. From left to right: 1.5 M NaCl, 2.0 M NaCl and 3.0 M NaCl. The 1.5 M solution does not gel the PVA, the 2.0 M solution and 3.0 M solution do gel the PVA. Note the progressive opacification of the 2.0 M gel and the shrinkage of the 3 M gel from the edges of the casette as the sample compacts with time (indicated with arrow).

The physical appearance of the hydrogel depends on the molarity of the solution into which the PVA solution is immersed. FIG. 3 demonstrates the progression of the gelation of the PVA hydrogel during exposure to NaCl solutions near the "theta" concentration. As exposure time increases, the PVA solution becomes stiff and opaque for the solutions at or above the theta concentration and temperature. For solutions appreciably below the theta concentration, little or no gelling is apparent. Immersion of the PVA solution into the 50/50 water/methanol solution also resulted in the generation of a uniform PVA hydrogel.

FIG. 3 shows 10% PVA solution in dialyzer cassettes after 1 day (top) and 3 days (bottom) of immersion in curing solution. From left to right: 1.5 M NaCl, 2.0 M NaCl and 3.0 M NaCl. The 1.5 M solution does not gel the PVA, but the 2.0 M solution and 3.0 M solution do gel the PVA. Note the progressive opacification of the 2.0 M gel and the shrinkage of the 3 M gel from the edges of the cassette as the sample compacts with time (indicated with arrow).

Figure 4:
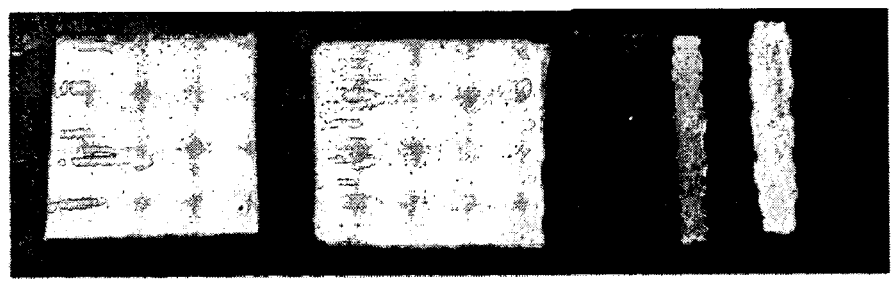
FIG. 4 shows a uniform thetagel in accordance with a preferred embodiment of the present invention. PVA gels generated by immersion in 3.0 M (left image of each pair) and 2.0 M (right image) NaCl curing solution. Note that the gels are uniform and opaque. The gel exposed to 3.0 M NaCl swells less and is more compact following equilibration in deionized water.

FIG. 4 demonstrates the difference between 10% PVA exposed to 3.0 M and 2.0 M solutions for 3 days (after photographed subsequent equilibration in deionized water). PVA gels were generated by immersion in 3.0 M (left image of each pair) and 2.0 M (right image) NaCl immersion solution. Note that the gels are uniform and opaque. The gel exposed to 3.0 M NaCl swells less and is more compact following equilibration in deionized water. The hydrogels that result are uniform and opaque. The PVA exposed to 2.0 M NaCl is more highly hydrated than that exposed to the 3.0 M NaCl. The increased swelling is an indication that the density of physical crosslinks is lower in the gel exposed to the 2 M NaCl solution. Thus, gels formed in this way are "tunable" with respect to mechanical properties. Further, gradient gels can be made using the method through manipulation of the spatial NaCl concentration.

Figure 5:
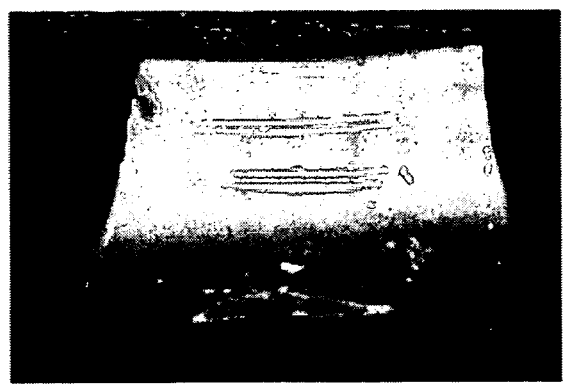
FIG. 5 shows an example of a gradient gel in accordance with a preferred embodiment of the present invention using a 10% PVA solution exposed to spatially varying NaCl concentration. Note the variation in both the translucency of the gel and in the swelling ratio.

FIG. 5 shows a hydrogel formed from a 10% PVA solution that was exposed to a spatially varying NaCl concentration. Note, the variation in both the translucency of the gel and in the swelling ratio. The opaque part of the gel was exposed to 3.0 M NaCl while the clear part was exposed to a concentration below the theta concentration (2.0 M at room temperature). The ability to generate a gradient is relevant to the generation of a total disk replacement nucleoplasty, with a rigid outer layer (annulus fibrosis) and a softer center (nucleus pulposus).

Differential Scanning Calorimetry

Figure 6:
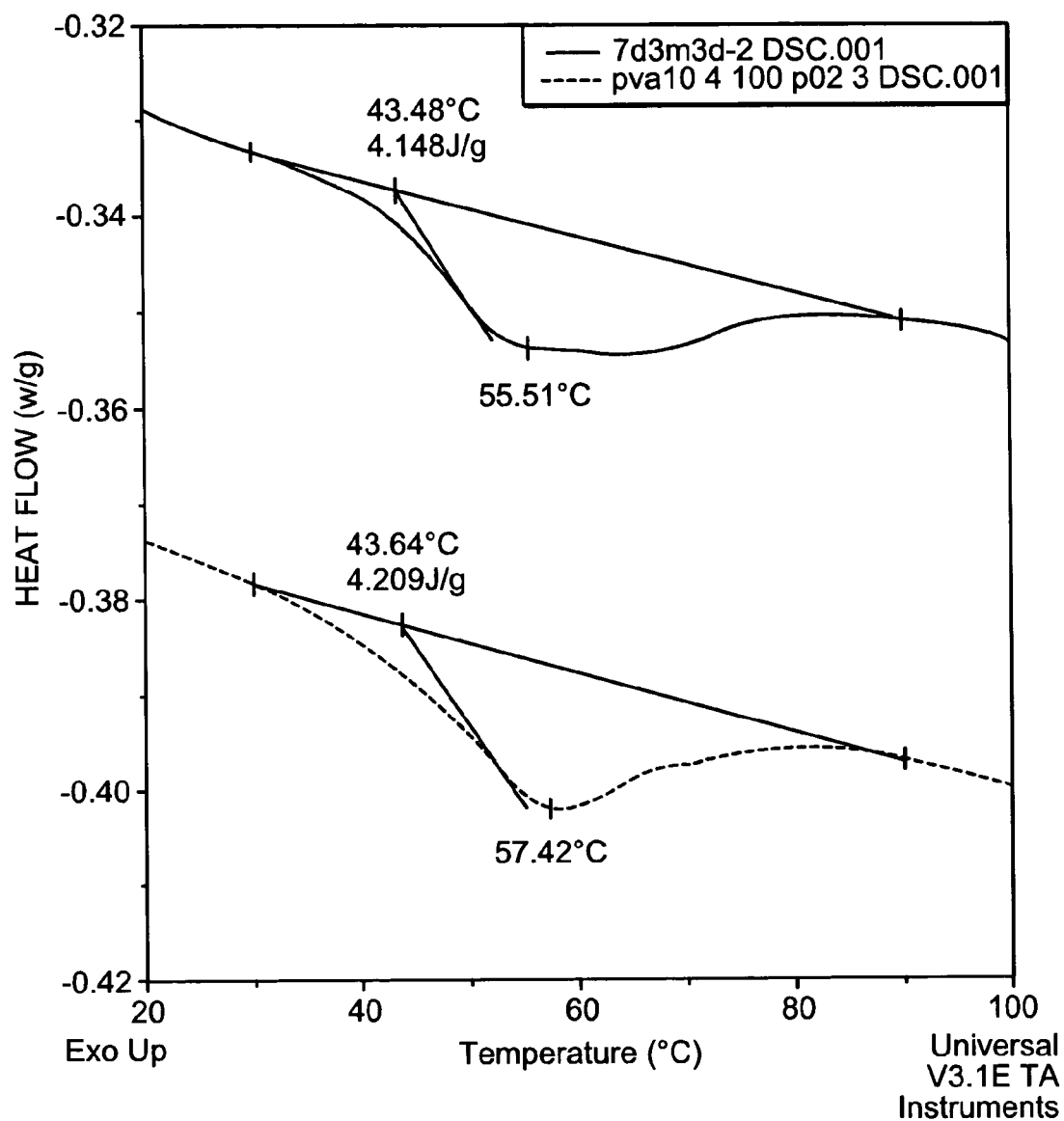
FIG. 6 shows a differential scanning calorimetry (DSC) thermogram comparing the results obtained with a thermally cycled PVA cryogel and the "thetagel" in accordance with a preferred embodiment of the present invention. The solid line is indicative of 10% PVA immersed in 3.0 M NaCl for 3 days; the dashed line is indicative of 10% PVA thermally cycled 4 times from 10 degrees Celsius to −20 degrees Celsius with a warming rate of 0.02 degrees Celsius/min.

For thermally cycled PVA gels, an endotherm between 30 degrees Celsius and 90 degrees Celsius represents the energy required to disrupt the physical crosslinks formed during the thermal processing. For PVA thetagels in accordance with a preferred embodiment, a similar endotherm was present. FIG. 6 compares the DSC thermogram of a thermally cycled PVA cryogel and a PVA hydrogel formed in 3.0M NaCl. The transitions have similar melting endotherms and occur at virtually the same temperature.

The enthalpy change of this endothermic transition gives a good indication of the amount of crosslinking in the gel as a result of the solution conditions. For a 10% PVA solution for example the enthalpy change obtained after immersion for 3 days in a 2.0M solution of NaCl was 16.9 J/g. In contrast the same initial PVA solution yielded an enthalpy change of 19.9 J/g after 3 days in a 3M solution. This result indicates that solution concentration and soak time both positively impact the amount of physical crosslinking in the gel.

Gravimetric Swell Ratio

Figure 7:
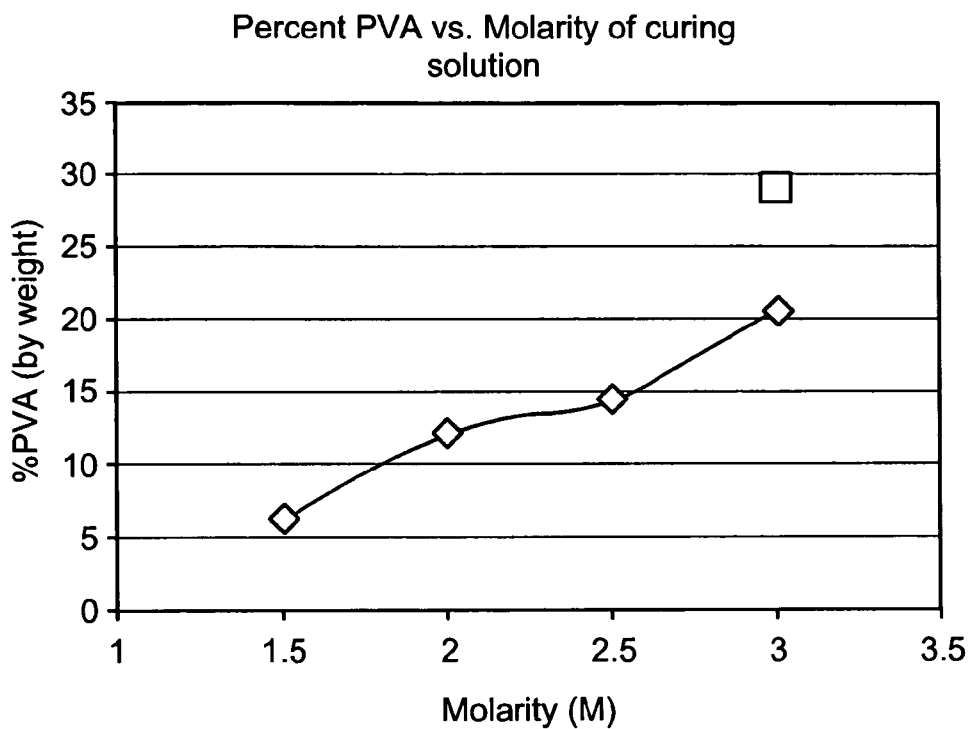
FIG. 7 graphically illustrates the relationship between the percentage of PVA in PVA hydrogels that were fully equilibrated in deionized water after being gelled in immersion solutions of different molarities in accordance with a preferred embodiment of the present invention. The connected points represent measurements of 10% PVA immersed for 3 days, the single point represents an initial solution of 20% PVA solution immersed in 3 M NaCl for 12 days. For the 20% PVA solution, the 3 day value of swelling ratio and percentage of PVA matched that of the 10% PVA solution (not shown). After 12 days of immersion in 3 M NaCl (and 5 days of equilibration in deionized water), the 20% PVA solution formed a gel that was 29% PVA.
Figure 8:
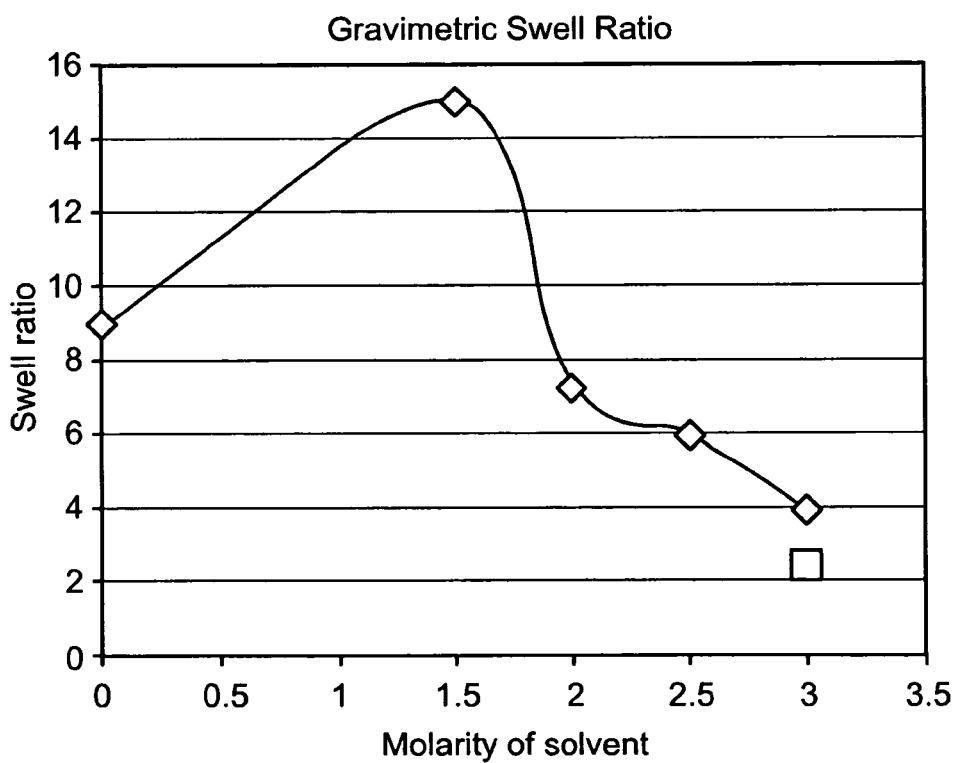
FIG. 8 graphically illustrates the gravimetric swelling ratio for PVA hydrogels that were fully equilibrated in deionized water after being gelled in immersion solutions of different molarities in accordance with a preferred embodiment of the present invention. The connected points represent measurements of 10% PVA immersed for 3 days, the single point represents an initial solution of 20% PVA solution immersed in 3 M NaCl for 12 days. For the 20% PVA solution, the 3 day value of swelling ratio and percentage of PVA matched that of the 10% PVA solution (not shown).

In a preferred embodiment, increasing the molarity of NaCl in the solvent increases the amount of PVA present in the hydrogel per unit mass. FIG. 7 shows the relationship between the percentage of PVA in the gels (fully equilibrated in deionized water) and the molarity of the solution in which they were cured. Because the PVA is not rigidly held in the dialysis cassette, it is free to expand or contract under the influence of the local forces on the PVA during the gelation process. It is therefore possible for the final PVA concentration to exceed that of the initial PVA solution if the PVA gel has collapsed. FIG. 8 shows the gravimetric swelling ratio for PVA cured in solutions of varying NaCl molarity. For the 20% PVA solution, the 3 day value of swelling ratio and percentage of PVA matched that of the 10% PVA solution (not shown). After 12 days of immersion in 3 M NaCl (and 5 days of equilibration in deionized water), the 20% PVA solution formed a gel that was 29% PVA.

Dynamic Mechanical Analysis

Figure 9:
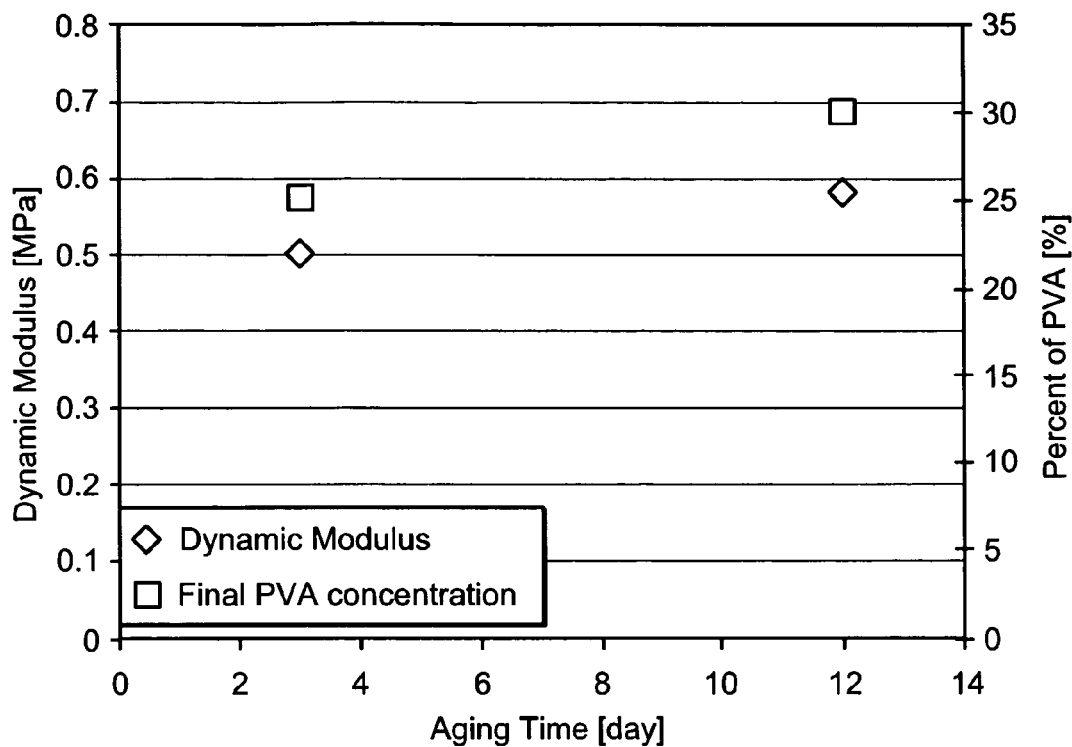
FIG. 9 shows the dynamic modulus of PVA thetagel at 3 M NaCl, 20% initial PVA concentration and 1 N static load versus aging time in days in accordance with a preferred embodiment of the present invention.
Figure 10:
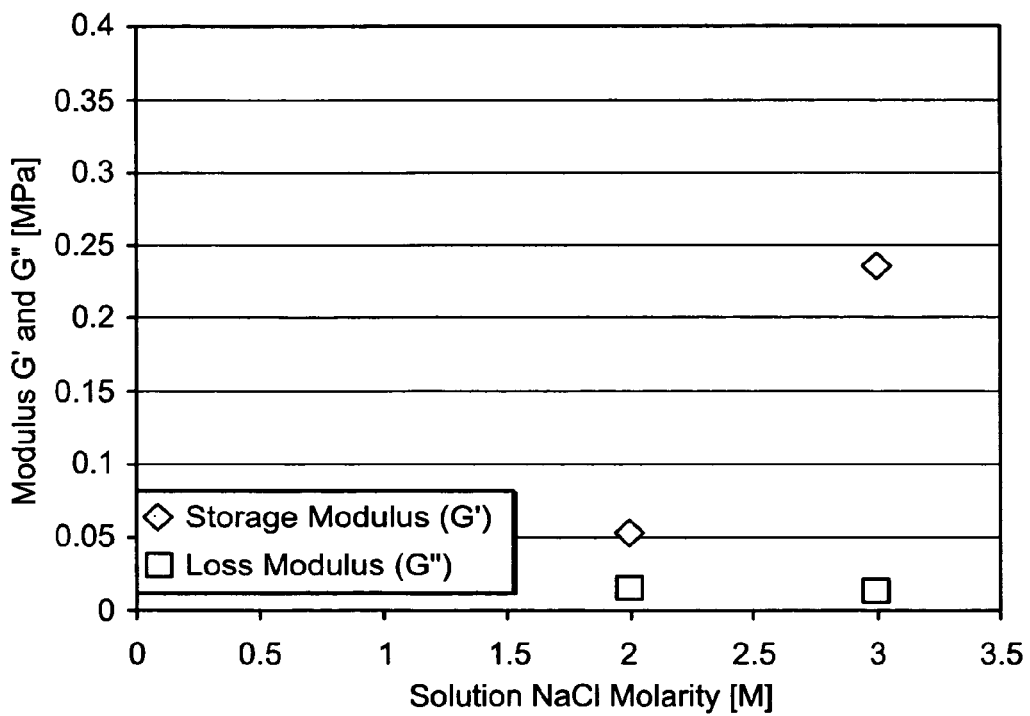
FIG. 10 shows the complex modulus (Storage (G') and Loss (G") Modulus) of PVA thetagel at 20% initial PVA concentration and 0.25 N static load against solution molarity (2M and 3M NaCl) in accordance with a preferred embodiment of the present invention.
Figure 11:
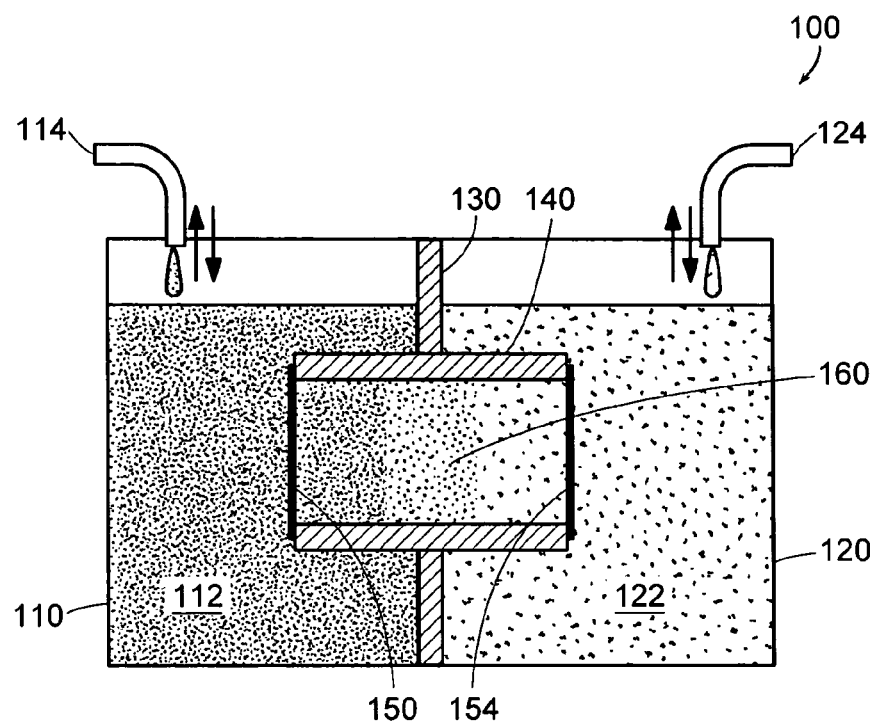
FIG. 11 is a schematic diagram of an "Ussing" type chamber used to create a gradient gel 160 in accordance with a preferred embodiment of the present invention.

In a preferred embodiment, the solution conditions and time of aging have a marked effect on the visible structure of the gels, and on their thermal properties. Both effects suggest that there is likely to be an influence on the mechanical properties as well. This supposition is born out by qualitative examination of the samples, but for more rigorous analysis mechanical testing was performed on the samples using DMA. FIGS. 9 and 10 present data taken from three of the samples. FIG. 9 shows that the complex modulus of the sample increases with aging (keeping all other solution conditions constant). In fact, this increase in the modulus is also paralleled by a densification of the final PVA gel. FIG. 10 examines the change in modulus corresponding to the change in solution molarity (once again keeping all other parameters constant). In this FIG. 10, there is a clear indication that the storage (i.e., elastic component) modulus rises sharply as the solution molarity is increased (remember at room temperature 2 M NaCl is approximately a theta solvent) whereas the loss (i.e., damping) modulus is barely affected.

Cryogels have a fairly low resolution with regard to their final properties because each thermal cycle produces a dramatic change in the material properties of the gel. The thetagels produced demonstrate that the concentration of the solvent produces a monotonic decrease in swelling ratio once the "theta" value is passed (See FIG. 7). Thus, the ultimate crosslink density can be fine tuned in proportion to the resolution achievable in the solvent concentration. For example, for the 10% PVA solution immersed in NaCl, the weight percentage of PVA in the final gel varies at a rate of about 7% per mole NaCl.

In preferred embodiments, the PVA thetagels can be made that exhibit a smooth gradient in spatial properties. Gradient properties cannot easily be manufactured in cryogels. Instead, the usual approach is to generate an array of stacked lamellae independently that must be joined in dissolved PVA and then cycled again. Sharp differences in modulus in such an array create a material with undesirable mechanical properties and with inhomogeneous interfaces. A preferred embodiment includes a composite annulus fibrosus/nucleus pulposus implant, that benefit from technology enabling a smooth gradient in mechanical properties, wherein a central lower modulus "pulposus" provides adequate compressive strength and a higher modulus peripheral "annulus" minimizes creep and undesirable distortion.

Modulus enhancement: Incorporation of ionic species. For thetagels produced in NaCl, it is possible to include natural (hyaluronic acid) or synthetic (PAA) polymers to create gels with strain variable compressive moduli Gelling a PVA/PAA solution in strong NaCl will shield the ionizable charges in the PAA while the PVA is crosslinked around the collapsed PAA. Re-equilibration in deionized water will allow expansion of the PAA and pre-stress the PVA matrix. The resulting construct has a very different mechanical compressive modulus due to the repulsion of the fixed charges on the incorporated PAA.

Generating gradient thetagel

In another preferred embodiment, to make the gradient thetagel: 10%, 20% and 30% solutions of 100 kg/mole PVA are made as described hereinbefore. A dialyzer cassette is split in half and each half bonded to one side of a 1×1×1 cm plexiglass box that is filled with the 10% PVA solution. The sealed box is placed into a temperature controlled "Ussing" style chamber where it is subjected to a constant 4 molar NaCl concentration difference (see FIG. 10). After the number of days where further changes in the gel are insignificant, the gradient gel is removed from the chamber and placed in deionized water for five days prior to further testing. Resulting gels are tested as described hereinbefore.

In another embodiment, spatial gradient can be generated using temporal oscillations in concentration. The concentration in the chamber can be modulated temporally to provide a gel, having a softer interior region than the peripheral region where a higher crosslinking occurs.

The chamber 100 includes a cartridge 140 containing a gel 160. The chamber can be divided into sub-chambers or regions including two immersion solvents 112 and 122. In a preferred embodiment, the solvents have the same concentration. In another preferred embodiment, the immersion solvents have different concentrations that cause a spatial gradient in the gel. Membranes 150, 154 are permeable membranes that allow the immersion solvents to selectively flow into the vinyl polymer solution. Membrane 130 provides an impermeable barrier to the flow of any solvent.

Dehydration

Preferred embodiments of the present invention are directed at controllably structuring gels. In a particular embodiment, in order to promote smooth dehydration and to homogenize the physical crosslinking of the PVA thetagel, the gel or solution of PVA may be immersed in a series of solutions, or in a bath of smoothly changing solvent quality, each with a higher Flory interaction parameter than the previous solution. This prevents the local "crashing out" of PVA at the surface directly in contact with the immersion solution. The term "crashing out" as used herein is associated with a phenomenon akin to precipitation because of the Flory interaction parameter. The polymer chains prefer to associate with themselves instead of the solvent as the Flory interaction parameter is above the theta point and thus precipitate or crash out.

In one preferred embodiment, a thetagel may be created by first immersing the contained PVA solution into a solvent which has a Flory interaction parameter that is higher than the theta point for the PVA solvent pair. After a period of time the contained PVA is immersed in another solvent, which has a Flory interaction parameter lower than the theta point for the PVA solvent pair. The process can continue with immersion of the contained PVA in solutions having successive decreases in the Flory interaction parameter until the desired interaction parameter value for the final gel is reached.

A method to form a thetagel in accordance with a preferred embodiment of the present invention includes immersing contained 5-20% PVA in DI, followed by immersion for a range of 1 hour to 1 day in 2.0 M NaCl, followed by immersion for a time period ranging between 1 hour to 1 day in 3.0 M NaCl, followed by immersion for a time period of 1 hour to 1 day in 4.0 M NaCl, and followed by immersion for a time period ranging from 1 hour to 1 day in 5.0 M NaCl.

In another preferred embodiment, the PVA solution may be subjected to a gradually changing solvent quality through a similar range of electrolyte concentrations by the gradual addition of a concentrated NaCl solution to a DI water bath such that the change of the salt concentration is slower, or equal to, the diffusion process into the gel.

A method in accordance with a preferred embodiment includes immersing contained 5-20% PVA in 1 liter of 1.5 M NaCl, and adding 6 M NaCl at a rate of 0.5 ml per minute to raise the electrolyte concentration at a rate of 0.0038 M/min and reaching 5 M NaCl after approximately 12 hours.

In another embodiment, the PVA solution may be subjected to one or many freeze-thaw cycles to fix the gel into a particular shape. It may then be immersed in a series of solutions having successively higher Flory interaction parameters until the final desired Flory parameter is reached.

A method in accordance with a preferred embodiment includes dissolving 5-20% PVA in DI, subjecting the solution to freeze-thaw cycles (approximately 1-8 cycles), and subsequently for a period ranging between 1 hour to 1 day, immersing the resultant gel in 2.0 M NaCl. The method further includes immersing the PVA gel for a time period of 1 hour to 1 day in 3.0 M NaCl, followed by immersion for a time period ranging from 1 hour to 1 day in 4.0 M NaCl and subsequently immersing for a time period of 1 hour to 1 day in 5.0 M NaCl.

In an alternate preferred embodiment, a method to form a gel includes dissolving a 5-20% PVA in DI, adding NaCl to the PVA solution to generate a concentration from 0.01 to 2 M NaCl in the PVA solution and then subjecting the PVA/NaCl solution to between 1 to 8 freeze-thaw cycles.

Nanostructuring

Polyvinyl alcohol gel is an extremely biocompatible material that can be made reasonably stiff without the use of chemical crosslinking or irradiation. However, the material properties of the PVA do not match the requirements of materials for use in load bearing applications such as, for example, artificial articular cartilage or intervertebral disks. A nanostructural enhancement of polymer systems in accordance with a preferred embodiment of the present invention indicates that PVA gels, which are already nearly suitable for use in load bearing orthopedic devices, may become viable candidates for such applications.

Nanostructuring polyvinyl alcohol theta and hydrogels—particles. The addition of particles to polymeric materials can improve the mechanical and thermal properties of the resulting material when compared to formulations of the neat polymer. Recently, it has been shown that the addition of nanoparticles to polymers can generate similar enhancements in the material properties, but with much lower particulate concentrations than those required of micron sized particles. This is particularly true when the material properties are dependent on surface area. In accordance with preferred embodiments, to strengthen polyvinyl alcohol thetagels or hydrogels, the dispersion of uncharged nanoscale particles or charged nanoscale particles with uniform or spatially varying surface charges into the solution prior to gelation enhances the mechanical and thermal properties of the final gel. Nanoscale particles, if dispersed properly, provide regular nucleation sites for physical crosslinking by adsorbing PVA chains to their surfaces in accordance with a preferred embodiment of the present invention. As in rubber toughened plastics, these nanoparticles also act as stress concentrators, thus toughening the gel. Nanoscale particles that may enhance the properties of PVA gels are, for example, clays (for example, but not limited to, laponite, montmorillonite), fumed silica, titanium dioxide or hydroxyapatite. Surface treatments and modifications, such as end grafting of polymers also adjust the way in which the particles interact with the polymer gel matrix in accordance with a preferred embodiment of the present invention. These particles may also be biologically active, such as, for example, capable of releasing drugs to promote growth, or reduce inflammation. Nanostructuring is not limited to thetagels in accordance with a preferred embodiment of the present invention. However, the thetagels in accordance with the present invention allow the formation of physical crosslinks around charged particles under solution conditions where the debye length is reduced compared to the working solution. Thus when the gel is replaced in the working solution of lower electrolyte concentration the particles interact through electrostatic forces and add compressive strength to PVA thetagels as compared to PVA freeze-thaw gels.

In one embodiment, nanoparticles are dispersed into solutions of PVA. The solvent may be water, DMSO, methanol or any other solution that exhibits a Flory interaction parameter that is lower than the theta point for the PVA solvent pair during solution preparation. The PVA/nanoparticle mixture is then subjected to at least one freeze-thaw cycle. Subsequent to the freeze-thaw cycling, the gelled PVA is immersed in a solvent that has a Flory interaction parameter near or higher than the theta point for the PVA/solvent pair to induce further physical crosslinking of the PVA/nanoparticle mixture.

A method in accordance with a preferred embodiment of the present invention includes mixing 5-20% PVA in DI with 1-10% fumed silica, freeze-thawing (1-8 cycles) the solution, followed by immersion for a time period ranging from 1 hour to 5 days in 2-5 M NaCl.

In another embodiment, the PVA/nanoparticle mixture is gelled by immersion into a solvent that has a Flory interaction parameter near or higher than the theta point for the PVA/solvent pair to induce physical crosslinking of the PVA/nanoparticle mixture. No freeze-thaw cycling is necessary in this embodiment.

A method in accordance with a preferred embodiment of the present invention includes mixing 5-20% PVA in DI with 1-10% fumed silica, followed by immersion for a time period ranging from 1 hour to 5 days in 2-5 M NaCl.

In another embodiment, the composite gels resulting from the two examples described hereinbefore are subject to further freeze-thaw cycles.

In another embodiment, PVA solutions or gels containing nanoparticles are subject to the dehydration protocol as described hereinbefore. A method in accordance with a preferred embodiment of the present invention includes mixing 5-20% PVA in DI with 1-10% fumed silica, subjecting the solution for 1-8 cycles of freeze-thawing, followed by immersion for a time period ranging from 1 hour to 1 day in 2.0 M NaCl, followed by immersion for a time period ranging from 1 hour to 1 day in 3.0 M NaCl, followed by immersion for a time period ranging from 1 hour to 1 day in 4.0 M NaCl and subsequently followed by immersion for a time period ranging from 1 hour to 1 day in 5.0 M NaCl.

Nanostructuring polyvinyl alcohol thetagels and cryogels—functionalized molecular additives. The addition of particles to the PVA solution prior to gelation can provide enhancement of the thermal and mechanical properties of the gel. However, there is a class of molecular additives that can be functionalized to promote physical crosslinking and can simultaneously act as stress concentrators. Polyhedral oligomeric silsesquioxane (POSS) can enhance mechanical properties of polymeric materials. Since the POSS molecules can be functionalized, they can be tuned to associate with the PVA chains to enhance interchain crosslinking and to act as stress concentrators. Their extremely small size and large number of functionalized groups has the potential to provide better results than nanoparticle seeding.

All of the methods for generating thetagels or cryogels described hereinbefore may be applied to solutions containing dispersed functionalized POSS molecules. In one preferred embodiment, POSS functionalized to display negatively charged oxygen groups can be used to promote hydrogen bonding. The functionalized POSS is dispersed into aqueous PVA solution and subjected to theta or freeze-thaw gelation (ranges 0.01 mM to 1 M OctaTMA POSS (tetramethyl ammonium salt) and 5-20% PVA in solution).

In another preferred embodiment, POSS functionalized to display alcohol groups is dispersed into PVA and subjected to theta or freeze-thaw gelation (ranges 0.01 mM to 1 M Octahydroxypropyldimethylsilyl POSS and 5-20% PVA in solution)

In another embodiment, POSS functionalized to display at least one PVA chain and at least one carboxyl or sulfate group can be used to produce an extremely hydrophilic, tough artificial cartilage. The preferred POSS construct has at least one PVA chain at opposite corners of the POSS with the 6 remaining functional groups expressing sulfate or carboxyl groups. This structure can be "stitched" into the PVA gel network via the thetagel process or freeze-thawing to produce an artificial cartilage with tunable properties.

Figure 12:
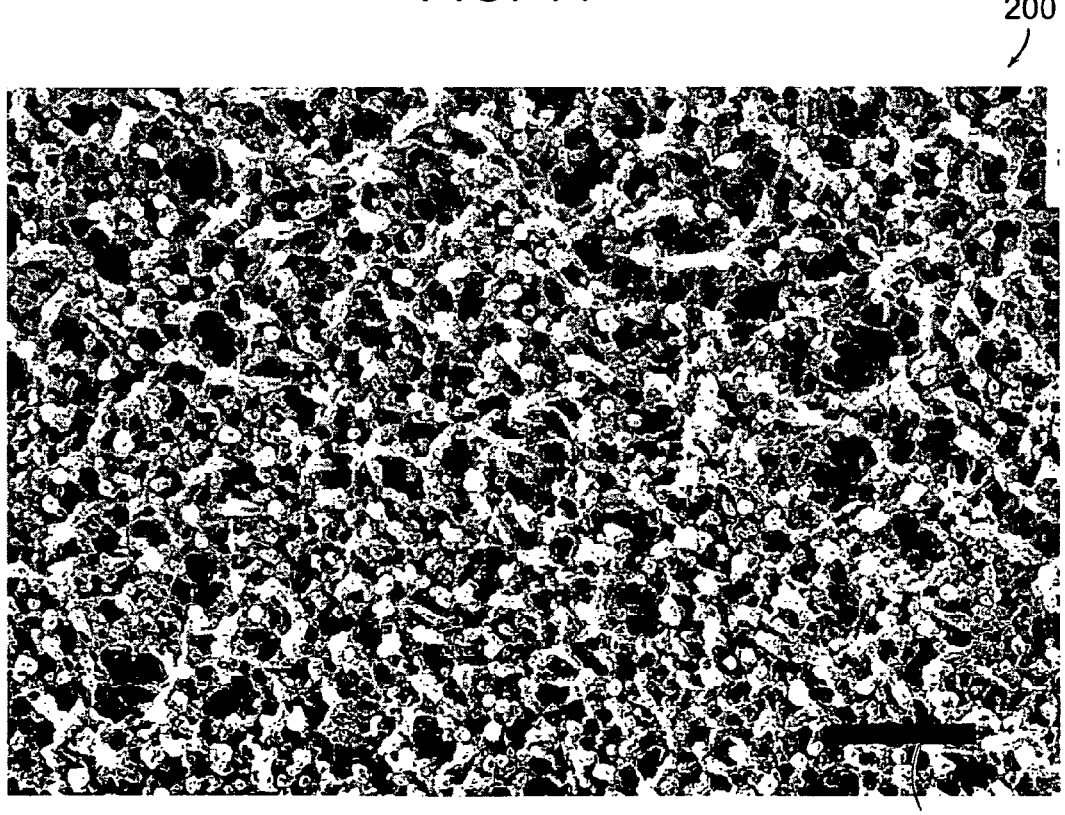
FIG. 12 illustrates a quick freeze deep etch (QFDE) image of PVA gel structure in accordance with a preferred embodiment of the present invention wherein the PVA gel is formed by immersion in 5 M NaCl for 3 days. The bar represents 100 nm.

FIG. 12 illustrates a quick freeze deep etch (QFDE) image of PVA gel structure in accordance with a preferred embodiment of the present invention wherein the PVA gel is formed by immersion in 5 M NaCl for 3 days. The bar represents 100 nm. QFDE preserves the gel structure in its hydrated state.

Figure 13A:
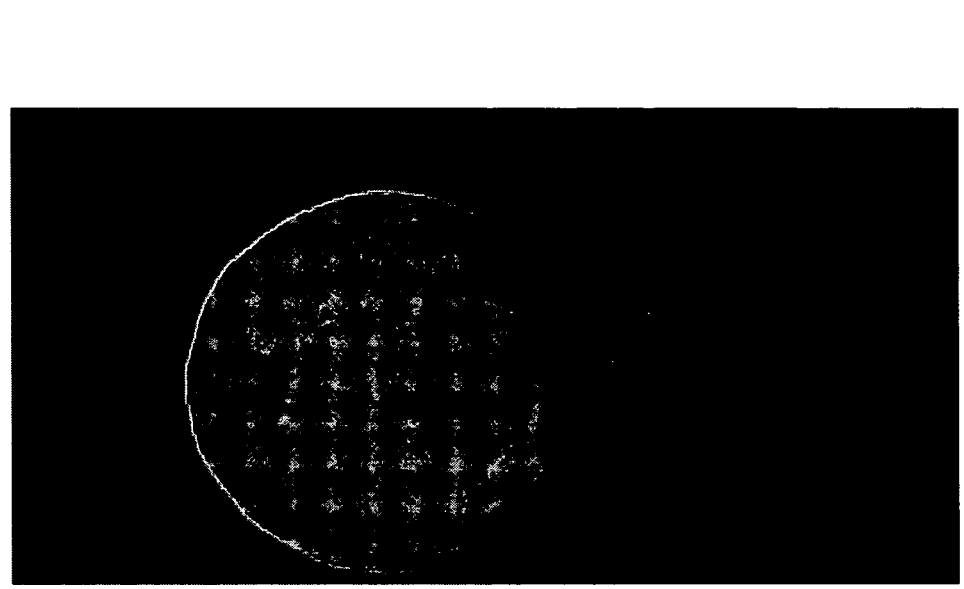
FIGS. 13A and 13B are a cross-sectional and a close-up view of the cross-section of a PVA gradient hydrogel, respectively, prepared by filling Plexiglass tubing with 10% PVA solution, performing one freeze thaw cycle (8 hours at −21° C.; 4 hours at room temperature) then immersing in 3 M NaCl bath for at least 3 days, then dehydrating in air for 60 hours and returning to dionized (DI) water in accordance with a preferred embodiment of the present invention.
Figure 13B:
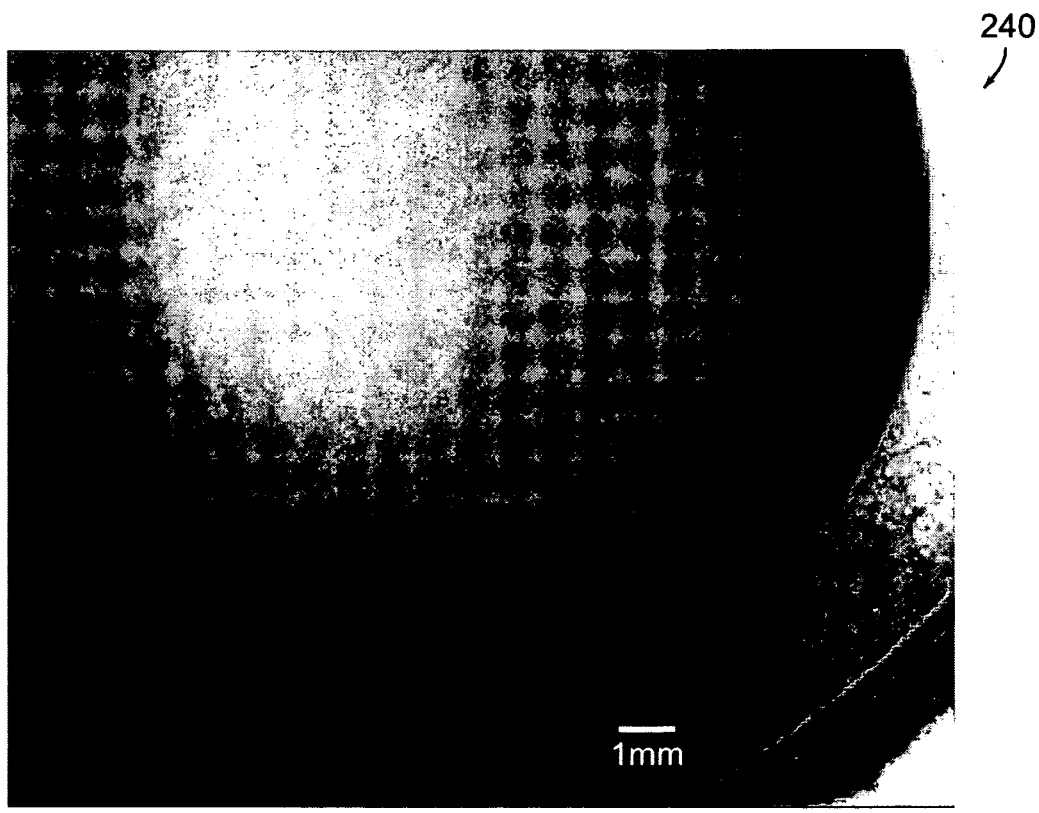

FIGS. 13A and 13B are a cross-sectional and a close-up view of the cross-section of a PVA gradient hydrogel, respectively, prepared by filling Plexiglass tubing with 10% PVA solution, performing one freeze thaw cycle (8 hours at −21° C.; 4 hours at room temperature) then immersing in 3 M NaCl bath for at least 3 days, and subsequently dehydrating in air for 60 hours and returning to deionized (DI) water in accordance with a preferred embodiment of the present invention. FIGS. 13A and 13B illustrate the presence of radial gradients in PVA induced by air dehydration.

Figure 14:
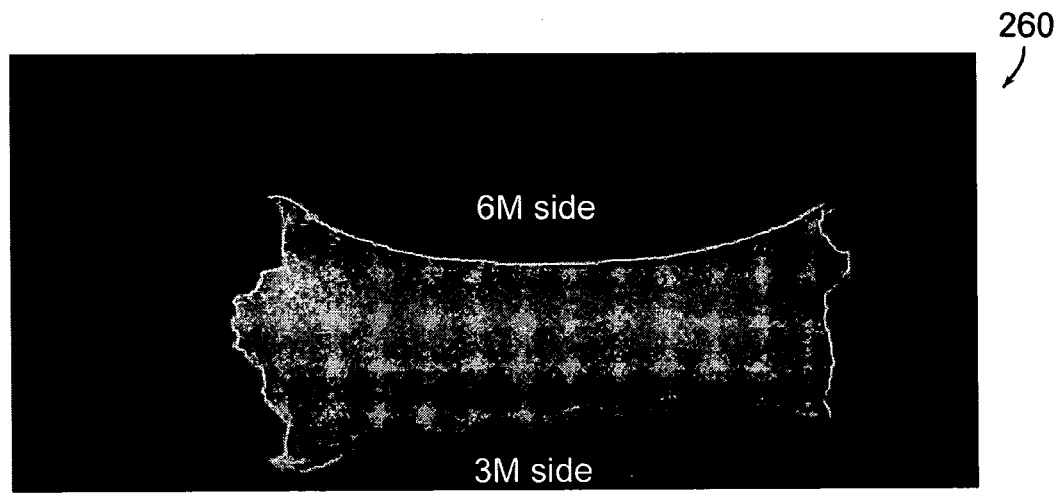
FIG. 14 illustrates a cross-sectional view of a PVA gradient hydrogel prepared by filling dialysis cartridge with 10% PVA solution, then immersing in a chamber having 3 M NaCl on one side and 6 M NaCl on the other side for 3 days in accordance with a preferred embodiment of the present invention.
Figure 15:
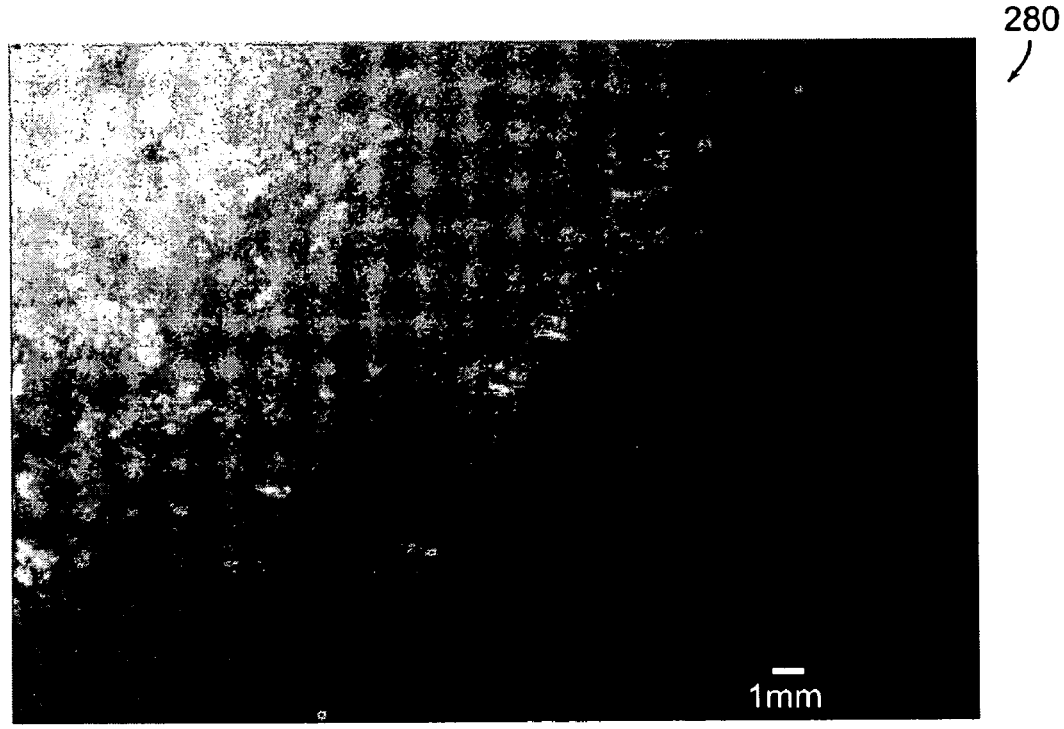
FIG. 15 illustrates a close-up view of the cross-section of the PVA gradient hydrogel of FIG. 14 on the 6 M NaCl side prepared by filling the dialysis cartridge with 10% PVA solution, and then immersing in a chamber with 3 M NaCl on one side and 6 M NaCl on the other for 3 days.

FIG. 14 illustrates a cross-sectional view of a PVA gradient hydrogel prepared by filling dialysis cartridge with 10% PVA solution, then immersing in a chamber having 3 M NaCl on one side and 6 M NaCl on the other side for 3 days in accordance with a preferred embodiment of the present invention. FIG. 15 illustrates a close-up view of the cross-section of the PVA gradient hydrogel of FIG. 14 on the 6 M NaCl side prepared by filling the dialysis cartridge with 10% PVA solution, and then immersing in a chamber with 3 M NaCl on one side and 6 M NaCl on the other for 3 days. FIGS. 14 and 15 illustrate the presence of linear gradients in PVA induced by static NaCl solution gradient.

Figure 16:
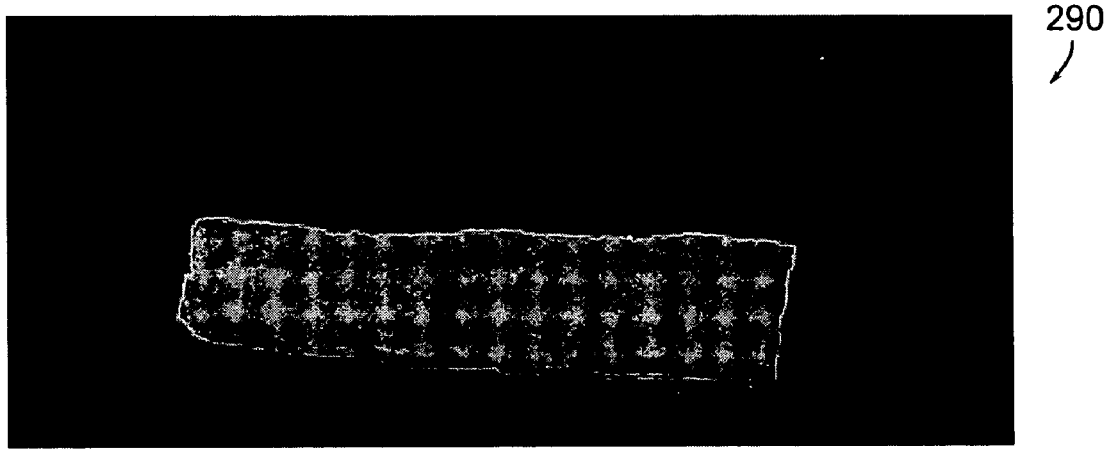
FIG. 16 illustrates a nanostructured PVA hydrogel prepared by mixing a solution of 10% PVA and 2 weight percent Laponite clay, subjecting to a 1 freeze-thaw cycle, then exposing to a 4 M NaCl solution for at least 3 days in accordance with a preferred embodiment of the present invention.

FIGS. 16-19 illustrate nanostructured PVA gels in accordance with preferred embodiments of the present invention. More particularly, FIG. 16 illustrates a nanostructured PVA hydrogel prepared by mixing a solution of 10% PVA and 2 weight percent Laponite clay, subjecting to a 1 freeze-thaw cycle, then exposing the solution to a 4 M NaCl solution for at least 3 days in accordance with a preferred embodiment of the present invention.

Figure 17:
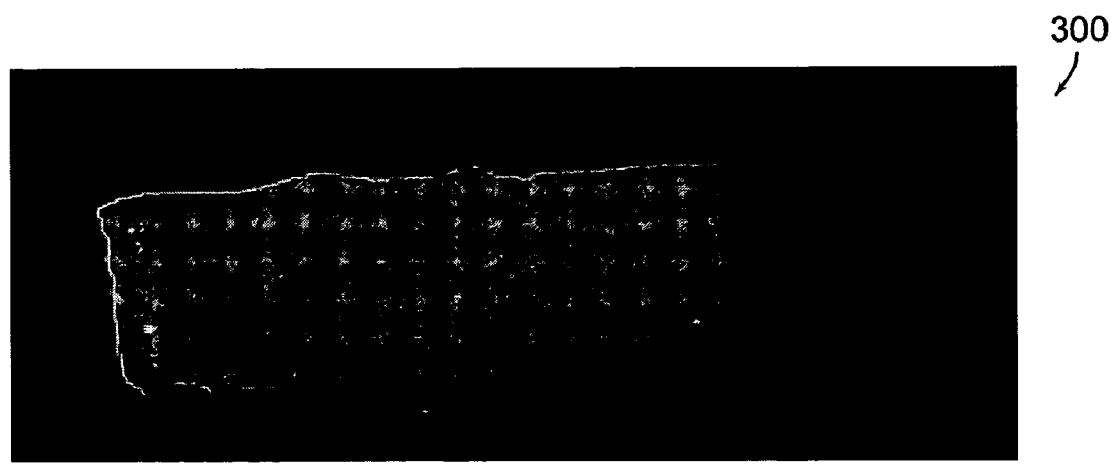
FIG. 17 illustrates a nanostructured PVA hydrogel prepared by mixing a solution of 10% PVA and 4 weight percent of silica, titrating to pH=3, subjecting to a 1 freeze-thaw cycle, then exposing to a 4 M NaCl solution for at least 3 days in accordance with a preferred embodiment of the present invention.

FIG. 17 illustrates a nanostructured PVA hydrogel prepared by mixing a solution of 10% PVA and 4 weight percent of silica, titrating to pH=3, subjecting to a 1 freeze-thaw cycle, then exposing to a 4 M NaCl solution for at least 3 days in accordance with a preferred embodiment of the present invention.

Figure 18:
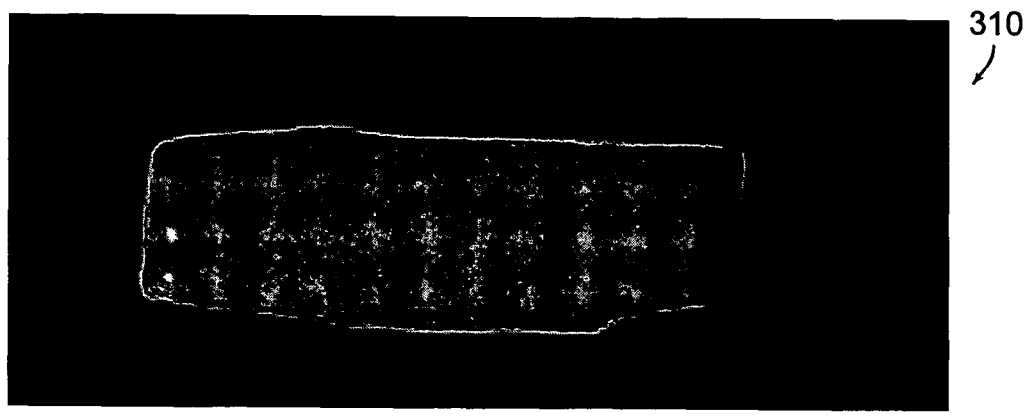
FIG. 18 illustrates a nanostructured PVA hydrogel prepared by mixing a solution of 10% PVA and 4 weight percent silica, titrating to pH=10, subjecting to 1 freeze-thaw cycle, then exposing to 4 M NaCl solution for at least 3 days in accordance with a preferred embodiment of the present invention.

FIG. 18 illustrates a nanostructured PVA hydrogel prepared by mixing a solution of 10% PVA and 4 weight percent silica, titrating to pH=10, subjecting to 1 freeze-thaw cycle, then exposing to 4 M NaCl solution for at least 3 days in accordance with a preferred embodiment of the present invention.

Figure 19:
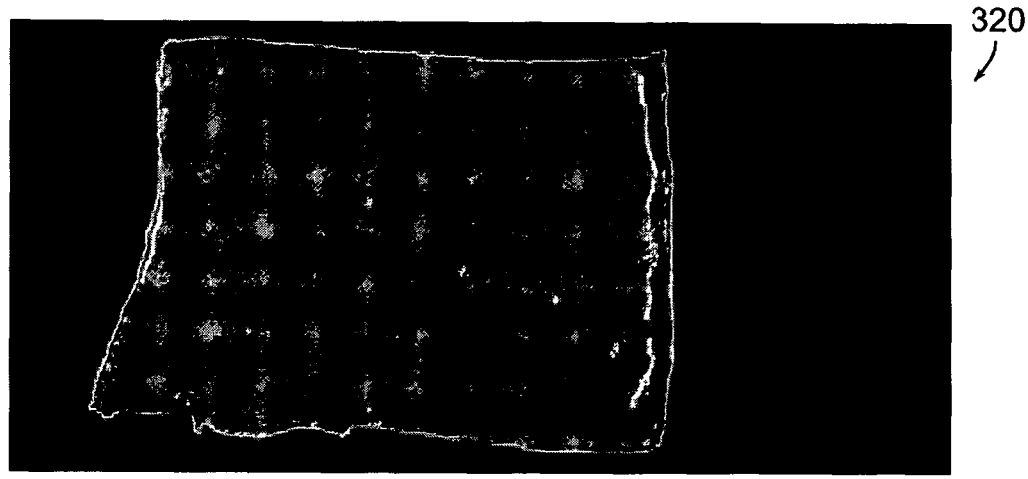
FIG. 19 illustrates a nanostructured PVA hydrogel prepared by mixing a solution of 10% PVA and an octatetramethylammonium polyhedral oligomeric silsesquioxane (OctaTMA POSS) in water, then subjecting to 1 freeze-thaw cycle in accordance with a preferred embodiment of the present invention.

FIG. 19 illustrates a nanostructured PVA hydrogel prepared by mixing a solution of 10% PVA and 0.001 M octaTMA POSS in water, then subjecting to 1 freeze-thaw cycle in accordance with a preferred embodiment of the present invention.

Figure 20:
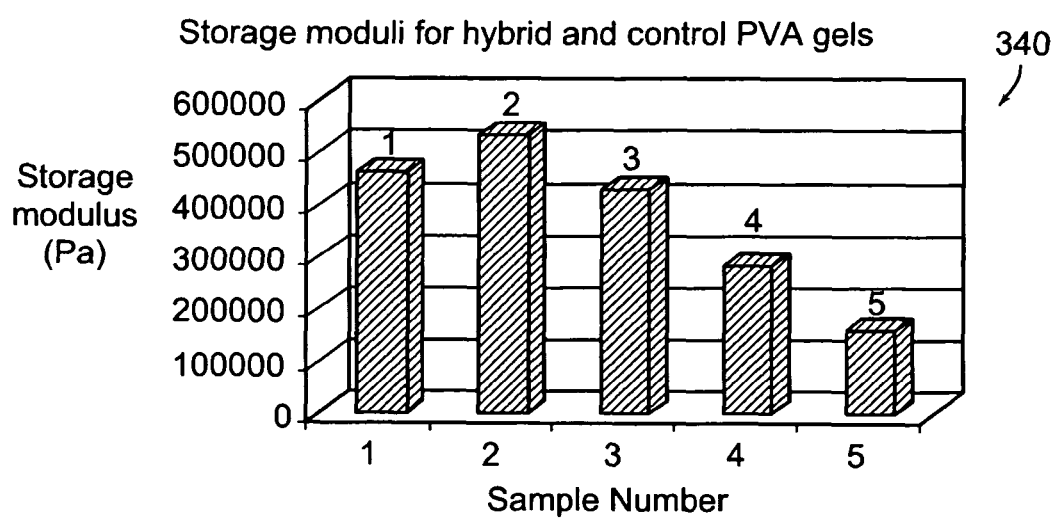
FIG. 20 graphically illustrates the storage modulus for hybrid and control PVA gels in accordance with a preferred embodiment of the present invention.

FIG. 20 graphically illustrates storage moduli for hybrid and control PVA gels in accordance with preferred embodiments of the present invention. The graphs are results of DMA testing on 4% silica/PVA nanostructured gel having a pH=10 (sample number 1), 4% silica/PVA nanostructured gel having a pH=3 (sample number 2), 2% Laponite/PVA nanostructured gel (sample number 3), 0.001 M, 10% PVA+octaTMA POSS (sample number 4), and a control gel (sample number 5). All gels were subjected to 1 freeze-thaw cycle and then immersed in 3 M NaCl for three days. Prior to DMA testing the samples were equilibrated in DI water for at least 24 hours.

The claims should not be read as limited to the described order or elements unless stated to that effect. Therefore, all embodiments that come within the scope and spirit of the following claims and equivalents thereto are claimed as the invention.

We claim:

1. A method of controlling properties and forming a physically crosslinked, biocompatible hydrogel for a medical implant, wherein the method comprises the steps of:
   (a) dissolving vinyl polymer molecules in a first solution to form a vinyl polymer solution, wherein the first solution has a Flory interaction parameter (chi value) that is not sufficient for gelation;
   (b) contacting the vinyl polymer solution with a second solution in a controlled manner, wherein after the contacting the combination of both solutions has a Flory interaction parameter (chi value) that is sufficient for gelation in order to form a physically crosslinked, biocompatible hydrogel without chemical crosslinkers, irradiation or thermal cycling; and
   (c) providing the physically crosslinked, biocompatible hydrogel formed in step (b) for the medical implant, wherein the medical implant is a load bearing or non-load bearing material for replacement, repair or enhancement of tissue.

2. The method according to claim 1, wherein the first solution comprises one or more selected from the group consisting of deionized water and dimethylsulfoxide.

3. The method according to claim 1, wherein the biocompatible polymer hydrogel is anisotropic in one or more properties.

4. The method of claim 1, wherein the vinyl polymer solution comprises about 1.0 to about 50.0 weight percent polyvinyl alcohol.

5. The method of claim 1, wherein after the contacting the Flory interaction parameter is 0.25 to 1.0.

6. The method of claim 1, wherein the vinyl polymer solution contains one or more non-gelling components.

7. The method of claim 1, wherein the vinyl polymer solution includes hyaluronic acid.

8. The method of claim 1, wherein the vinyl polymer solution includes polyacrylic acid.

9. The method of claim 1, wherein the vinyl polymer solution includes a therapeutic agent.

10. The method of claim 1, wherein the vinyl polymer solution is placed in a dialysis chamber having at least two sides to permit introduction of a solution having a higher Flory interaction parameter than the vinyl polymer solution, wherein each side is a dialysis membrane that controls the rate of introduction of the solution having a higher Flory interaction parameter.

11. The method of claim 10, wherein the vinyl polymer solution is separated by the membranes from at least two different solvents.

12. The method of claim 10, wherein the vinyl polymer solution is separated by the membranes from a second solvent and a third solvent.

13. The method according to claim 1, wherein the implant is selected from the group consisting of a hip implant, spine implant, knee implant, elbow implant, shoulder implant, wrist implant, hand implant, ankle implant, foot implant, jaw implant, breast implant and artificial cartilage.

14. A method of controlling properties and forming a physically crosslinked, biocompatible hydrogel for a medical device, wherein the method comprises the steps of:
   (a) dissolving vinyl polymer molecules in a first solution to form a vinyl polymer solution, wherein the first solution has a Flory interaction parameter (chi value) that is not sufficient for gelation;
   (b) contacting the vinyl polymer solution with a second solution in a controlled manner, wherein after the contacting the combination of both solutions has a Flory interaction parameter (chi value) that is sufficient for gelation in order to form a physically crosslinked, biocompatible hydrogel without chemical crosslinkers, irradiation or thermal cycling; and
   (c) providing the physically crosslinked, biocompatible hydrogel formed in step (b) for the medical device, wherein the medical device is for humans or animals.

15. The method according to claim 14, wherein the first solution comprises one or more selected from the group consisting of deionized water and dimethylsulfoxide.

16. The method according to claim 14, wherein the biocompatible polymer hydrogel is anisotropic in one or more properties.

17. The method of claim 14, wherein the vinyl polymer solution comprises about 1.0 to about 50.0 weight percent polyvinyl alcohol.

18. The method of claim 14, wherein after the contacting the Flory interaction parameter is 0.25 to 1.0.

19. The method of claim 14, wherein the vinyl polymer solution contains one or more non-gelling components.

20. The method of claim 14, wherein the vinyl polymer solution includes hyaluronic acid.

21. The method of claim 14, wherein the vinyl polymer solution includes polyacrylic acid.

22. The method of claim 14, wherein the vinyl polymer solution includes a therapeutic agent.

23. The method of claim 14, wherein the vinyl polymer solution is placed in a dialysis chamber having at least two sides to permit introduction of a solution having a higher Flory interaction parameter than the vinyl polymer solution, wherein each side is a dialysis membrane that controls the rate of introduction of the solution having a higher Flory interaction parameter.

24. The method of claim 23, wherein the vinyl polymer solution is separated by the membranes from at least two different solvents.

25. The method of claim 23, wherein the vinyl polymer solution is separated by the membranes from a second solvent and a third solvent.

26. The method according to claim 14, wherein the medical device is selected from the group consisting of active bandages, trans-epithelial drug delivery devices, drug release structure, filters, microfluidic devices, sponges, anti-adhesion materials, artificial vitreous humor, contact lens, and stents.

27. The method according to claim 1, wherein the implant is selected from the group consisting of a drug delivery device, drug release structure, filter, microfluidic device, sponge, anti-adhesion material, artificial vitreous humor, contact lens, breast implant, stent and artificial cartilage.

* * * * *